(12) United States Patent
Kent

(10) Patent No.: US 11,627,991 B2
(45) Date of Patent: Apr. 18, 2023

(54) ADJUSTABLE COMBINATION CLAMP ASSEMBLY

(71) Applicant: DePuy Synthes Products, Inc., Raynham, MA (US)

(72) Inventor: Todd J. Kent, Cherry Hill, NJ (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 314 days.

(21) Appl. No.: 16/592,165

(22) Filed: Oct. 3, 2019

(65) Prior Publication Data

US 2021/0100585 A1 Apr. 8, 2021

(51) Int. Cl.
*A61B 17/64* (2006.01)

(52) U.S. Cl.
CPC .................. *A61B 17/6416* (2013.01)

(58) Field of Classification Search
CPC ............ A61B 17/6416; A61B 17/6425; A61B 17/6433; A61B 17/6441; A61B 17/645; A61B 17/6466; A61B 17/6475; A61B 17/6483; A61B 17/6491
USPC .......................................................... 606/59
See application file for complete search history.

(56) References Cited

U.S. PATENT DOCUMENTS

| 4,456,005 A | * | 6/1984 | Lichty | A61B 17/8685 |
| | | | | 606/328 |
| 2007/0038217 A1 | * | 2/2007 | Brown | A61B 17/6466 |
| | | | | 606/57 |
| 2009/0088751 A1 | | 4/2009 | Mullaney | |
| 2011/0066151 A1 | * | 3/2011 | Murner | A61B 17/6466 |
| | | | | 606/54 |
| 2012/0004659 A1 | | 1/2012 | Miller et al. | |
| 2012/0289959 A1 | | 11/2012 | Miller | |
| 2012/0296335 A1 | | 11/2012 | Mullaney | |
| 2018/0103988 A1 | * | 4/2018 | Muniz | A61B 17/6425 |

FOREIGN PATENT DOCUMENTS

WO 2017/096336 A1 6/2017

* cited by examiner

*Primary Examiner* — Jan Christopher L Merene
(74) *Attorney, Agent, or Firm* — BakerHostetler

(57) ABSTRACT

A bone fixation clamp includes a first clamp assembly, a second clamp assembly, an inner locking member, and an outer locking assembly. The first and second clamp assemblies are transitionable between open and closed configurations. The inner locking member is transitionable between a locked position and an unlocked position. In the locked position the inner locking member engages the first clamp assembly substantially preventing the first clamp assembly from transitioning from the closed configuration to the open configuration. The outer locking assembly is transitionable between a locked position and an unlocked position. In the locked position the outer locking assembly engages the first clamp assembly and the second clamp assembly substantially preventing both the first clamp assembly from transitioning from the closed configuration to the open configuration and the second clamp assembly from transitioning from the closed configuration to the open configuration.

17 Claims, 17 Drawing Sheets

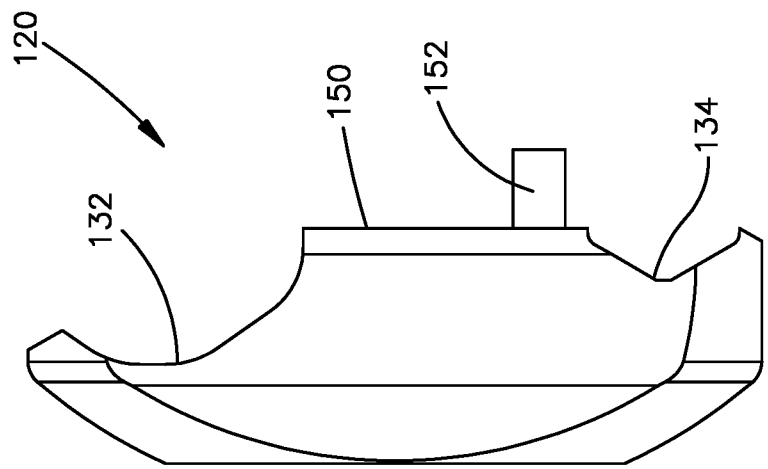
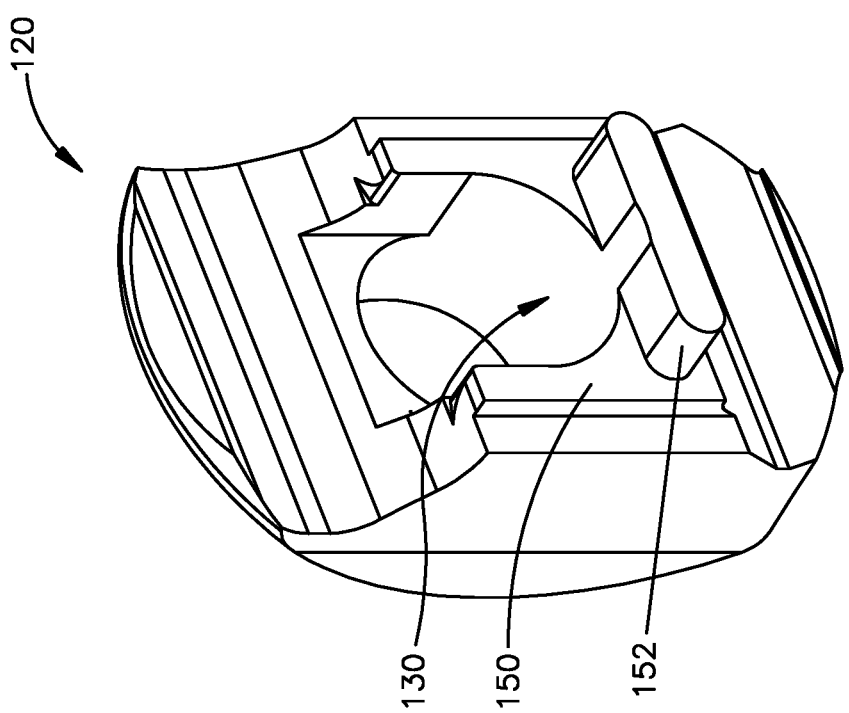

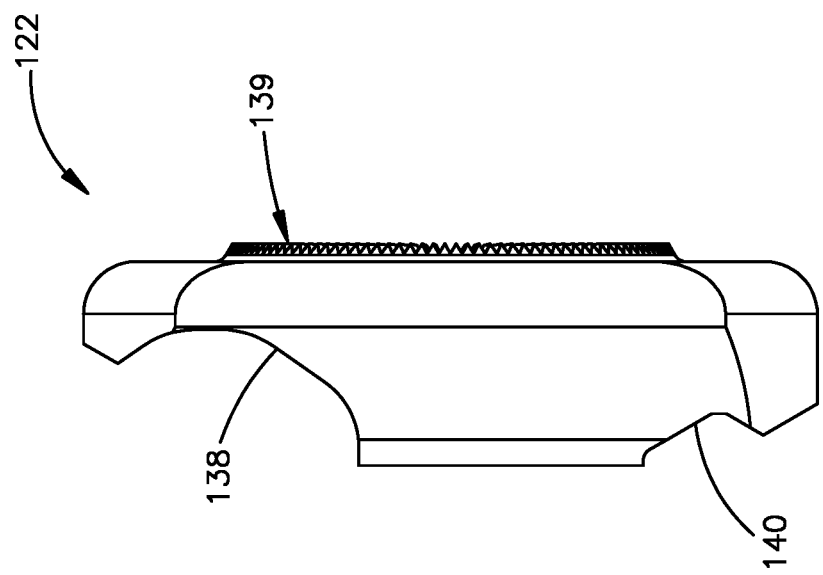
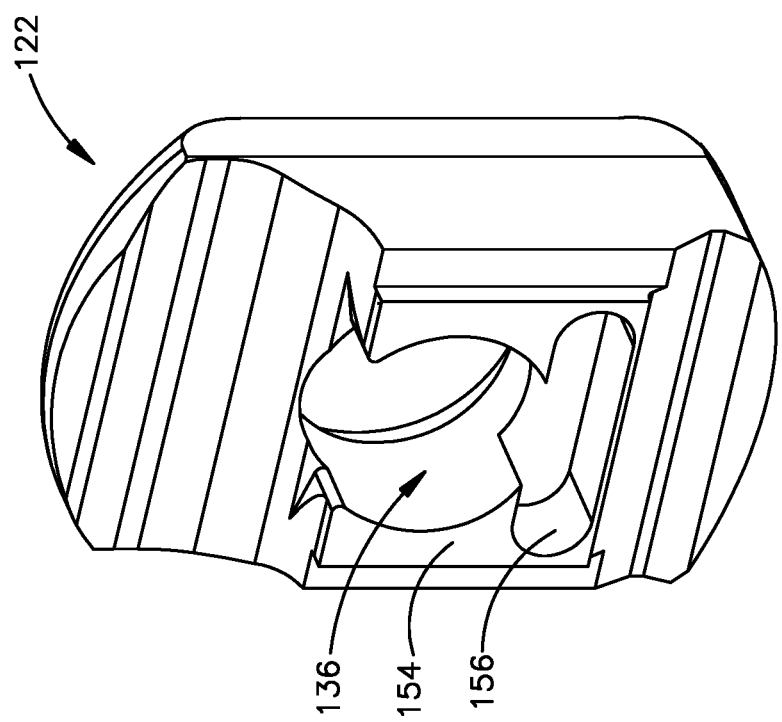
Fig.6B
Fig.6A

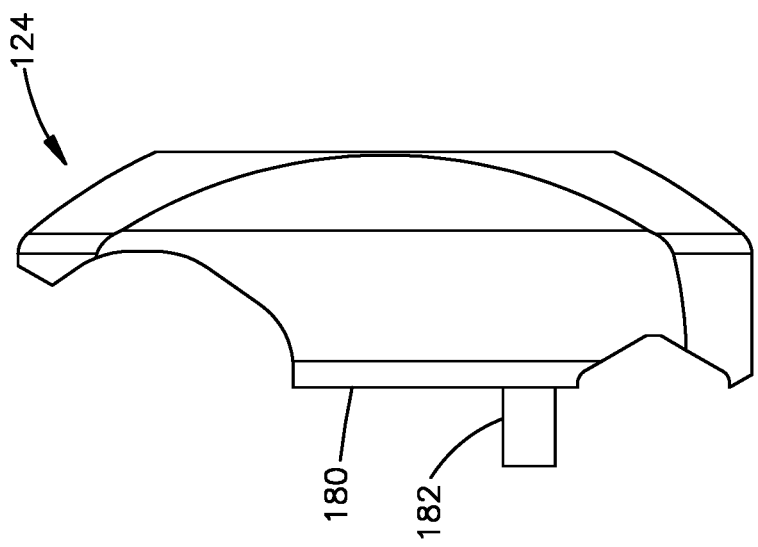
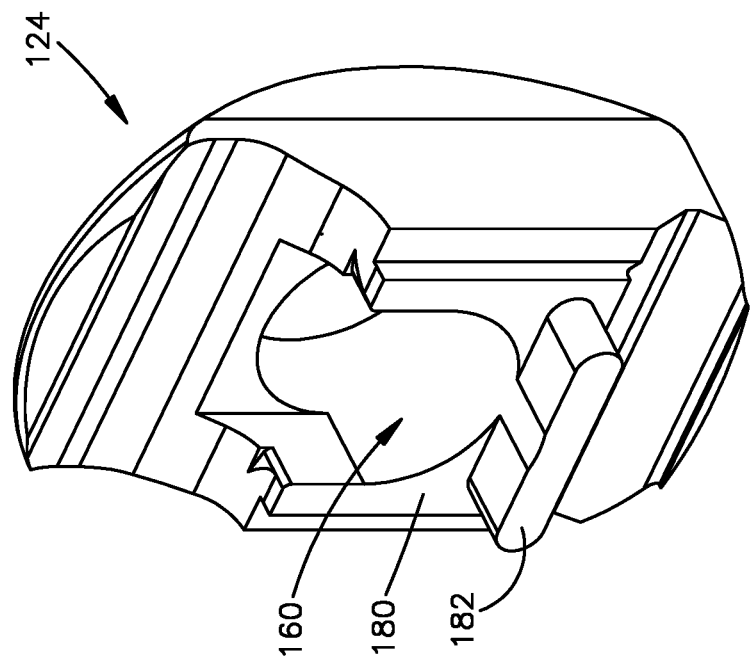

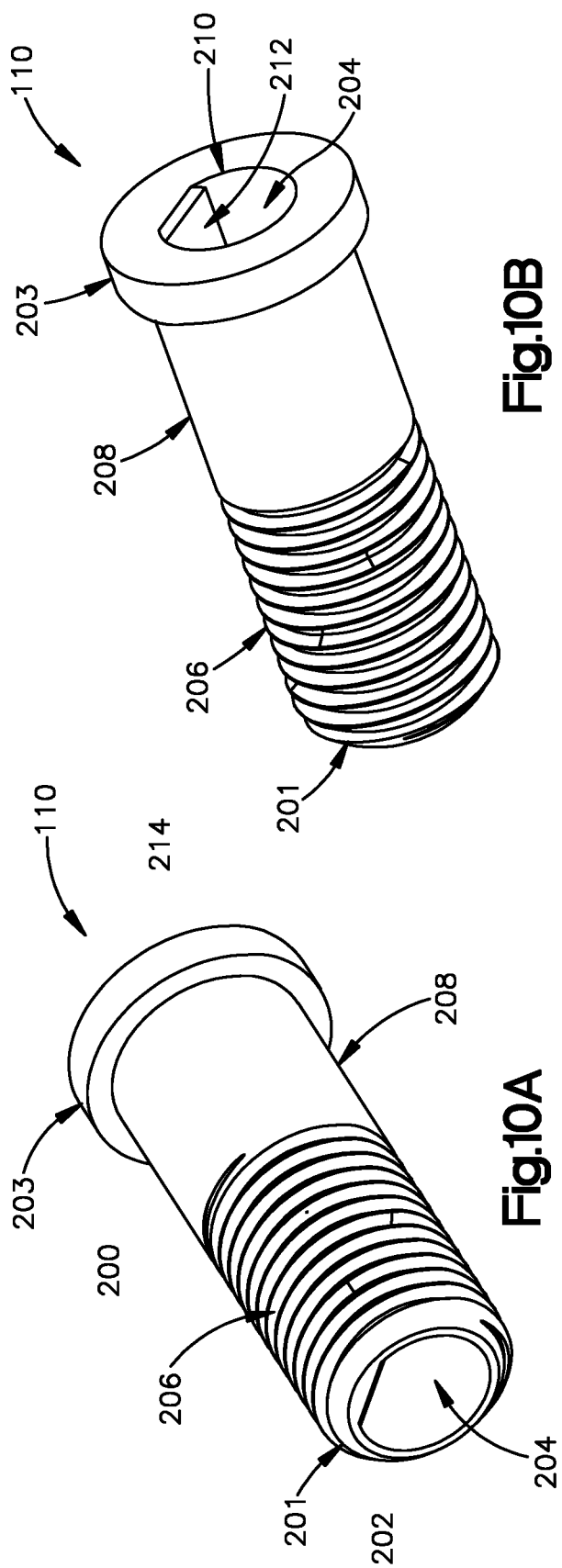
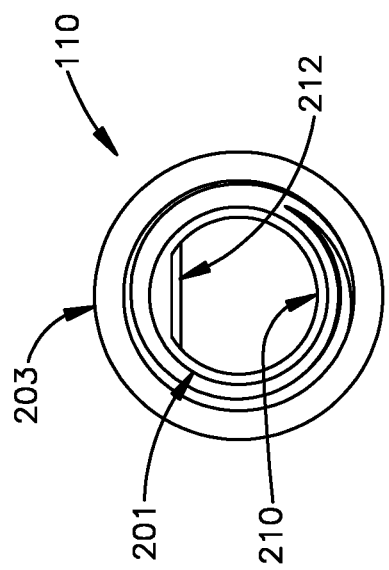
Fig.10B
Fig.10C
Fig.10A

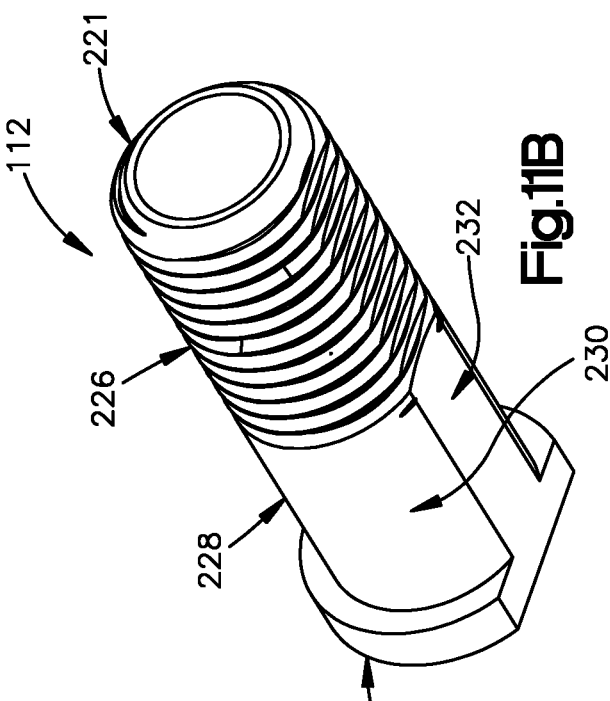
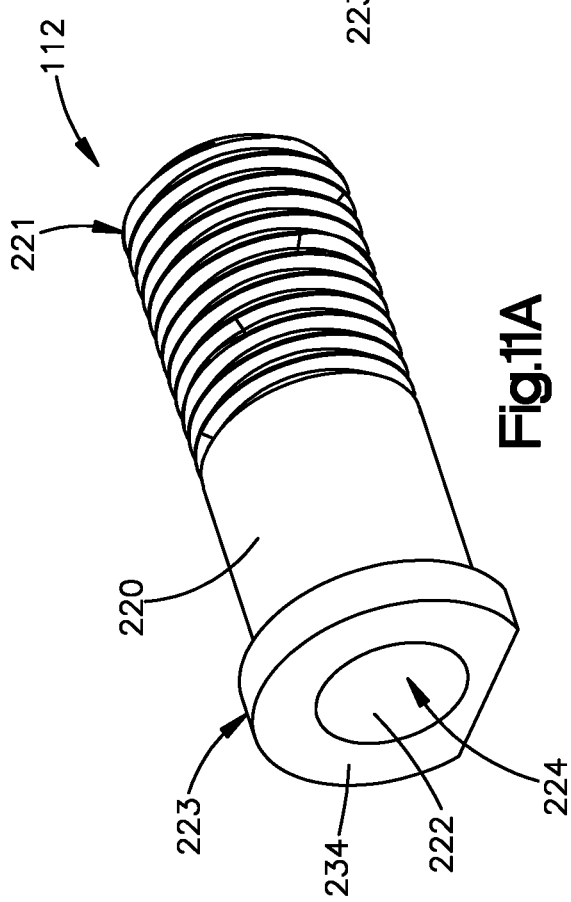
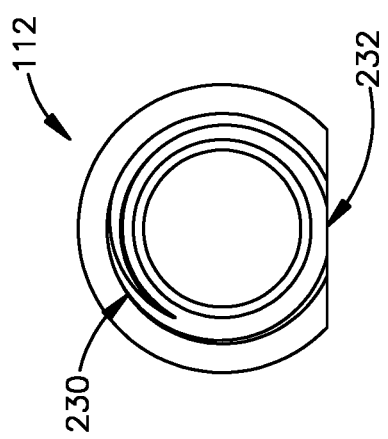

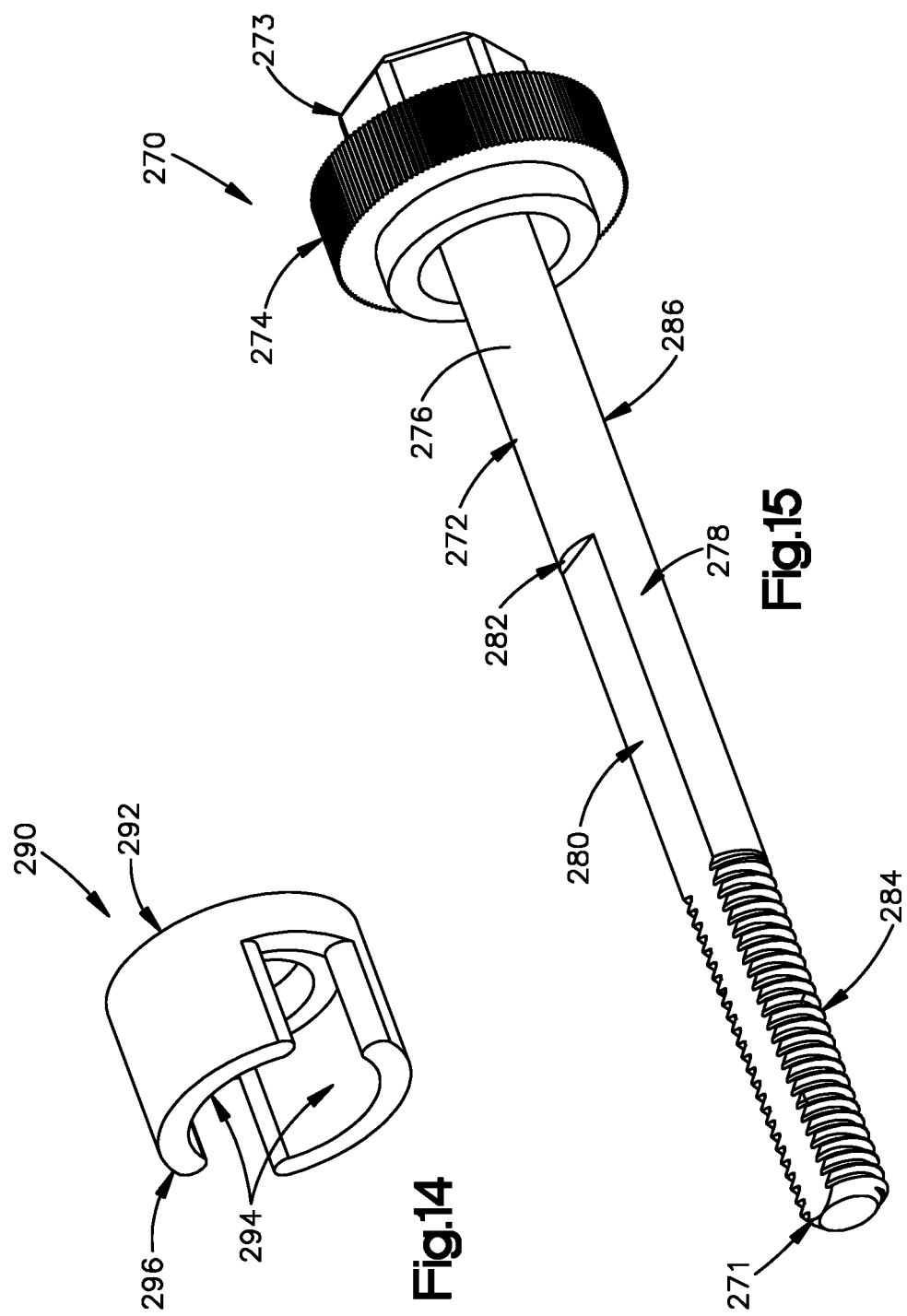

ADJUSTABLE COMBINATION CLAMP ASSEMBLY

TECHNICAL FIELD

This disclosure relates generally to fixation clamps and, more particularly, to an adjustable fixation clamp with multiple locking components.

BACKGROUND

Fixation clamps include clamping portions capable of securing rods, pins, bars, wires, screws, rings, or other like fixation components within. Fixation clamps can be rotated and/or moved to a desired position along the fixation component and locked into place. More than one fixation clamp can be used to secure several fixation components together to form a fixation system. Fixation systems can be used, for example, to connect two or more bone fragments to each other. These systems incorporate the screws, pins, wires, rods, bars, and/or rings to assist in healing of fractured bones and to assure proper alignment of bone. To provide for external fixation of, for example, a bone fracture, several points of fixation can be used. The fixation components are inserted into each bone fragment on opposite sides of a fracture. The components are connected to a fixation rod, pin, bar, or ring using fixation clamps, thereby creating an external fixation system. Such a configuration helps to prevent bone fragments from rotating and/or translating relative to each other.

Fixation clamps are secured to the fixation components for assembling the fixation system. Fixation clamps can include multiple clamp portions for affixing connecting multiple fixation components together. In some conventional fixation clamps, each clamping portion is independently locked and unlocked. If the components need to be adjusted, a user needs to unlock each clamping portion individually. In other conventional fixation clamps, the clamping portions are locked by a single locking mechanism. These fixation clamps require all the clamping portions to be unlocked in order to adjust one or more of the fixation components.

The foregoing background discussion is intended solely to aid the reader. It is not intended to limit the innovations described herein. Thus, the foregoing discussion should not be taken to indicate that any particular element of a prior system is unsuitable for use with the innovations described herein, nor is it intended to indicate that any element is essential in implementing the innovations described herein.

SUMMARY

An adjustable combination clamp with multiple locking capabilities is disclosed in the present application. The adjustable combination clamp allows for both individual and combination locking and unlocking of multiple clamping portions. In this manner, a user can apply the clamp by tightening a single control, but if adjustment of a single clamp portion is desired, a second control can individually control the single clamp portion.

An aspect of the present disclosure provides a clamp assembly. The clamp assembly comprises a first clamp sub-assembly, a second clamp sub-assembly, an inner locking member, and an outer locking member. The first clamp sub-assembly is transitionable between an open configuration and a closed configuration, and the second clamp sub-assembly is transitionable between an open configuration and a closed configuration. The second clamp sub-assembly is coupled to the first clamp sub-assembly. The inner locking member is transitionable between a locked position and an unlocked position. In the locked position the inner locking member engages the first clamp sub-assembly substantially preventing the first clamp sub-assembly from transitioning from the closed configuration to the open configuration. The outer locking member is transitionable between a locked position and an unlocked position. In the locked position the outer locking member engages the first clamp sub-assembly and the second clamp sub-assembly substantially preventing both the first clamp sub-assembly from transitioning from the closed configuration to the open configuration and the second clamp sub-assembly from transitioning from the closed configuration to the open configuration.

Another aspect of the present disclosure provides a clamp assembly. The clamp assembly comprises a clamp and inner and outer locking members. The clamp is transitionable between an open configuration and a closed configuration. The inner and outer locking members are configured to individually transition between locked positions and unlocked positions. In the locked position of either of the inner and outer locking members the clamp is substantially prevented from transitioning from the closed configuration to the open configuration. The inner locking member is coupled to the outer locking member such that the inner locking member is rotationally fixed relative to the outer locking member and the inner locking member is axially movable relative to the outer locking member.

Another aspect of the present disclosure provides a clamp assembly. The clamp assembly comprises first and second clamp sub-assemblies, first and second inner locking members, and an outer locking sub-assembly. The first clamp sub-assembly includes a first outer vise plate and a first inner vise plate. The first outer vise plate includes a first outer contacting surface having at least one first outer recess. The first inner vise plate includes a first inner contacting surface having at least one first inner recess. The first outer vise plate and the first inner vise plate are positioned adjacent to one another along a longitudinal axis of the clamp assembly such that at least one first receiving cavity is formed by the at least one first outer recess and the at least one first inner recess. The second clamp sub-assembly includes a second outer vise plate and a second inner vise plate. The second outer vise plate includes a second outer contacting surface having at least one second outer recess. The second inner vise plate includes a second inner contacting surface having at least one second inner recess. The second outer vise plate and the second inner vise plate are positioned adjacent to one another along the longitudinal axis such that at least one second receiving cavity is formed by the at least one second outer recess and the at least one second inner recess.

The first inner locking member is transitionable between a locked position and an unlocked position. In the locked position the first inner locking member substantially prevents the first outer vise plate from moving relative to the first inner vise plate along the longitudinal axis. The second inner locking member is transitionable between a locked position and an unlocked position. In the locked position the second inner locking member substantially prevents the second outer vise plate from moving relative to the second inner vise plate along the longitudinal axis. The outer locking sub-assembly is transitionable between a locked position and an unlocked position. In the locked position the outer locking sub-assembly substantially prevents both the first outer vise plate from moving relative to the first inner vise plate along the longitudinal axis and the second outer vise plate from moving relative to the second inner vise plate along the longitudinal axis.

This summary is provided to introduce a selection of concepts in a simplified form that are further described below in the Detailed Description section. This Summary is not intended to identify key features or essential features of the claimed subject matter, nor is it intended to be used to limit the scope of the claimed subject matter. Furthermore, the claimed subject matter is not constrained to limitations that solve any or all disadvantages noted in any part of this disclosure.

BRIEF DESCRIPTION OF THE DRAWINGS

The foregoing summary, as well as the following detailed description of illustrative embodiments of the present application, will be better understood when read in conjunction with the appended drawings. For the purposes of illustrating the present application, there are shown in the drawings illustrative embodiments of the disclosure. It should be understood, however, that the application is not limited to the precise arrangements and instrumentalities shown. In the drawings:

FIGS. 5A and 5B illustrate a top perspective view and a side view, respectively, of a first outer vise plate, according to aspects of this disclosure.

FIGS. 6A and 6B illustrate a top perspective view and a side view, respectively, of a first inner vise plate, respectively, according to aspects of this disclosure.

FIGS. 7A and 7B illustrate a top perspective view and a side view, respectively, of a second outer vise plate, according to aspects of this disclosure.

FIGS. 10A, 10B, and 10C illustrate a front perspective view, a back perspective view, and a front view, respectively, of a first sleeve, according to aspects of this disclosure.

FIGS. 11A, 11B, and 11C illustrate a front perspective view, a back perspective view, and a front view, respectively, of a second sleeve, according to aspects of this disclosure.

FIG. 14 illustrates a top perspective view of a second outer locking member, according to an aspect of this disclosure.

FIG. 15 illustrates a top perspective view of a second outer locking member, according to an aspect of this disclosure.

FIG. 20 illustrates a cross-sectional view of a clamp assembly with a first locking member and a second locking member in their respective locked positions, according to an aspect of this disclosure.

DETAILED DESCRIPTION

Figure 1:
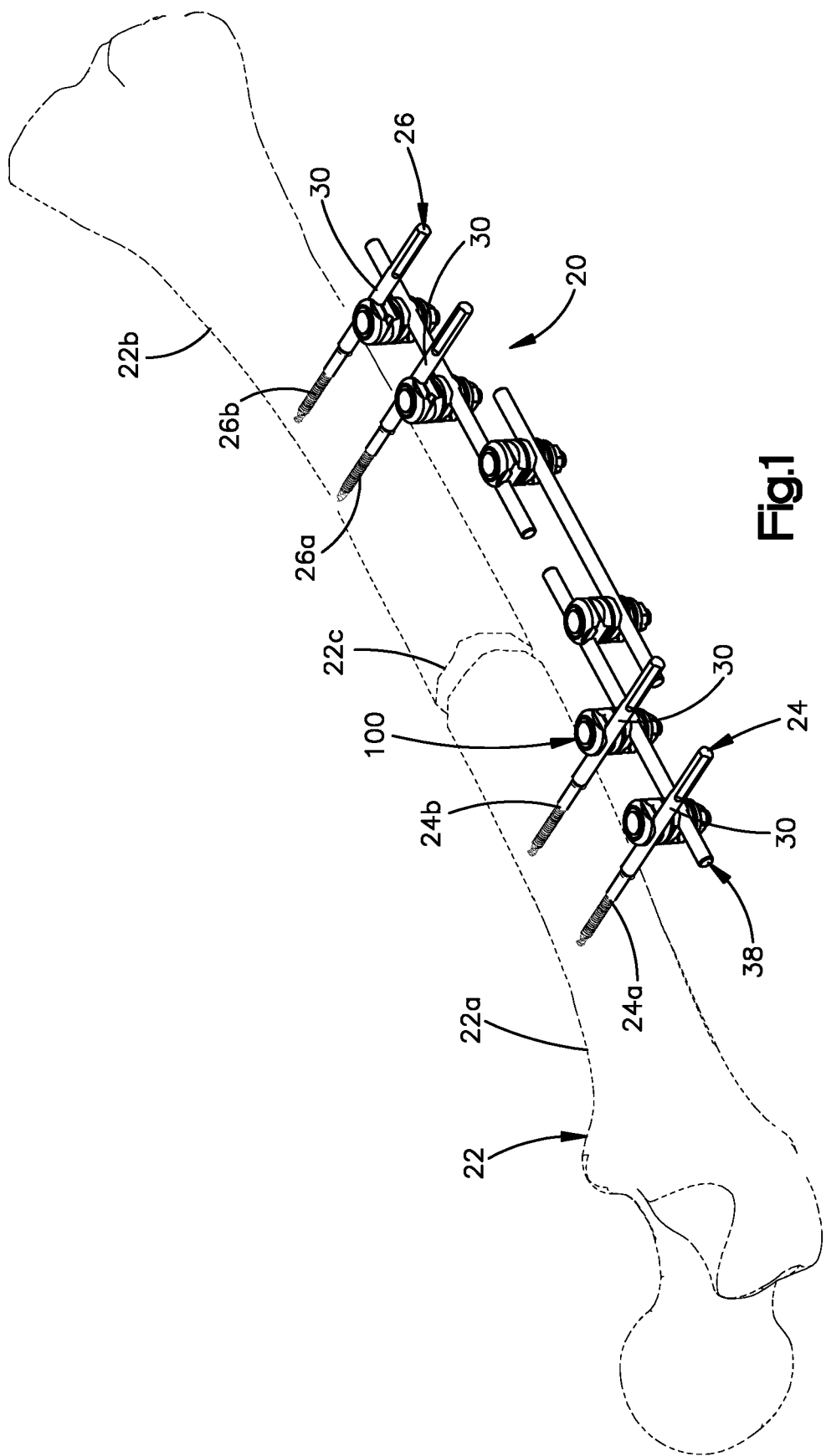
FIG. 1 illustrates an external fixation assembly anchored into a bone, according to an aspect of this disclosure.

Certain terminology used in this description is for convenience only and is not limiting. The words "top", "bottom", "distal", "proximal", "above", "below", "axial", "transverse", "circumferential," and "radial" designate directions in the drawings to which reference is made. The term "substantially" is intended to mean considerable in extent or largely but not necessarily wholly that which is specified. All ranges disclosed herein are inclusive of the recited endpoint and independently combinable (for example, the range of "from 2 grams to 10 grams" is inclusive of the endpoints, 2 grams and 10 grams, and all the intermediate values). The terminology includes the above-listed words, derivatives thereof and words of similar import.

Referring to FIG. 1, a bone implant, such as an external fixation system 20, is configured to stably support a first bone segment 22a relative to a second bone segment 22b. The first and second bone segments can be of the same bone or of different bones. In accordance with the illustrated embodiment, the first and second bone segments 22a-b are of a bone, such as a long bone 22, and are separated from each other by a bone gap 22c, such as a fracture, of the long bone 22. The external fixation system 20 can include at least one external fixation bone anchor 24 configured to attach to bone, for instance at the first bone segment 22a, and at least one external fixation bone anchor 26 configured to attach to bone, for instance at the second bone segment 22b. In accordance with the illustrated embodiment, the at least one bone anchor 24 can include first and second bone anchors 24a and 24b that are configured to attach to the same bone segment, for instance to the first bone segment 22a, and the at least one bone anchor 26 can include first and second bone anchors 26a and 26b that are configured to attach to the same bone segment, for instance to the second bone segment 22b.

The external fixation system 20 further includes at least one adjustable bone fixation clamp 100 configured to attach to a first one of the bone anchors 24a-b and 26a-b. The clamp 100 is further configured to attach to the at least one support rod 38 so as to fixedly secure the attached bone anchors to the at least one support rod 38. In accordance with the illustrated embodiment, the at least one clamp 100 is configured to attach to any of the bone anchors 24 and 26. In accordance with the illustrated embodiment, one clamp 100 is attached to the first bone anchor 24a and a second clamp 100 is attached to the second bone anchor 24b.

Further, in accordance with the illustrated embodiment, the at least one clamp 100 can include a first clamp and second clamp each configured to attach to any of the bone anchors 24 and 26 and/or the at least one support rod 38. As will be appreciated from the description below, clamp 100 is configured to attach to the bone anchors 24 and 26 at the respective shafts 30, for instance at the respective unthreaded external surfaces.

Figure 2:
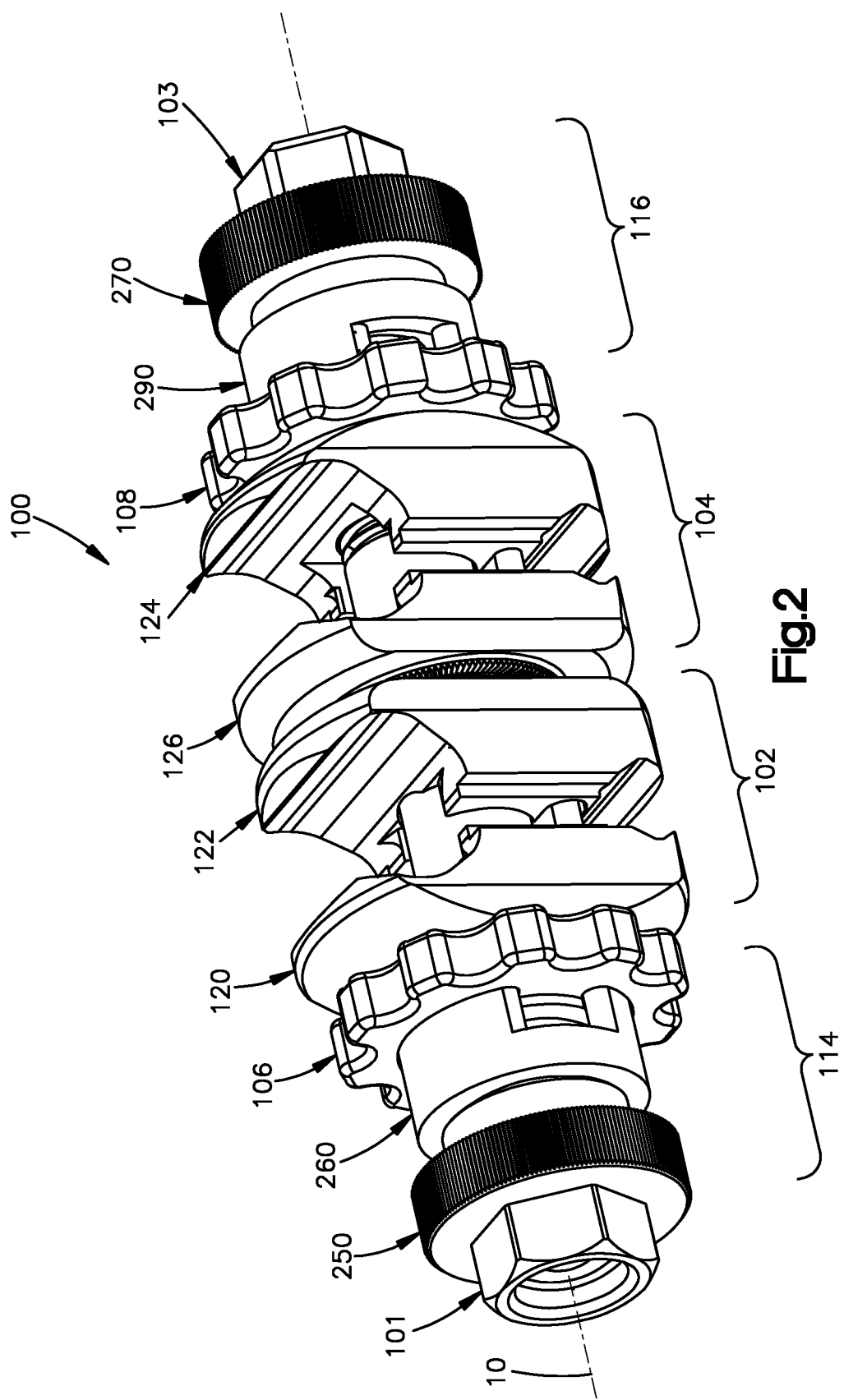
FIG. 2 illustrates a top perspective view of an adjustable combination clamp assembly, according to an aspect of this disclosure.
Figure 3:
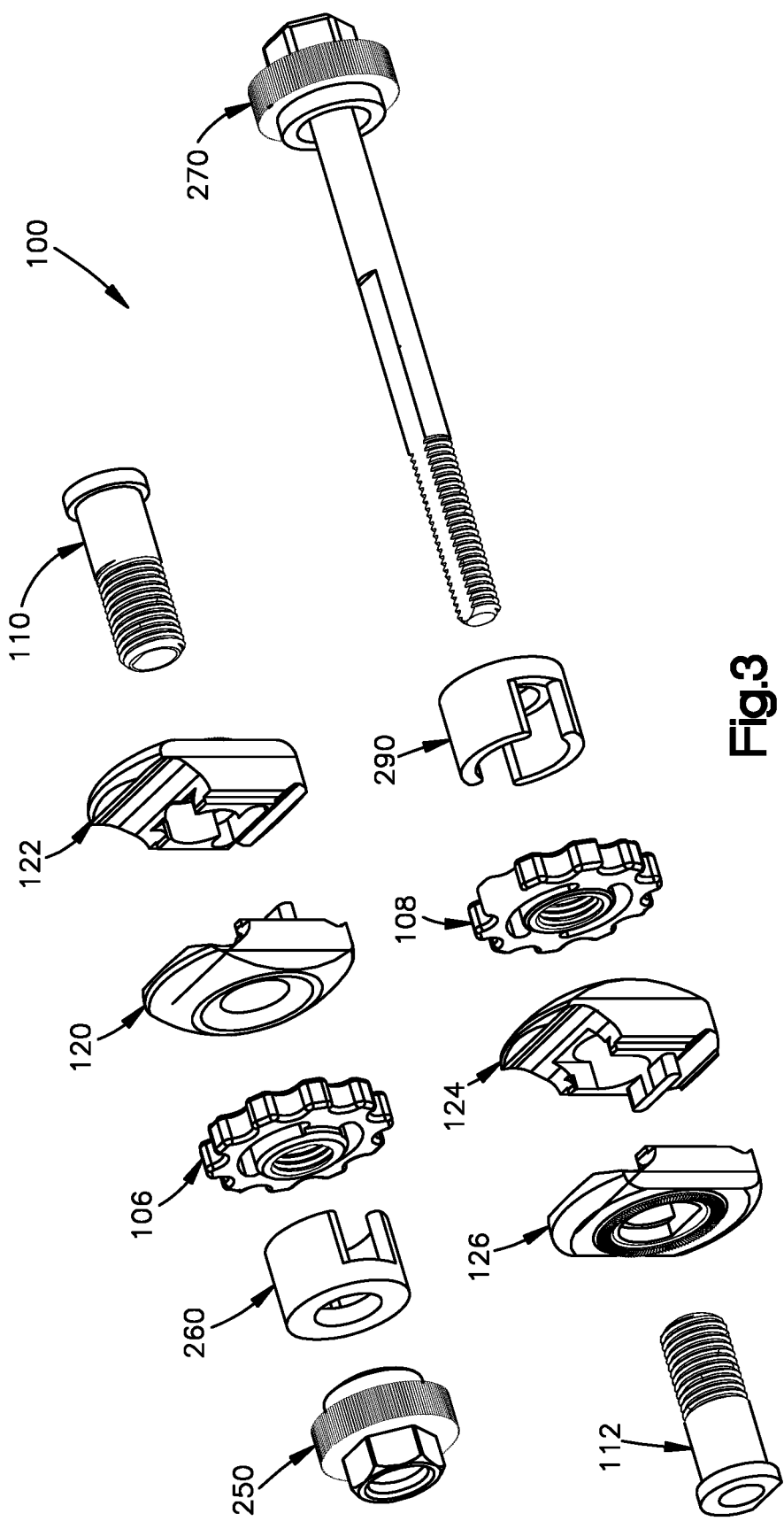
FIG. 3 illustrates a top perspective view of an exploded view of the adjustable combination clamp assembly shown in FIG. 2, according to an aspect of this disclosure.

FIGS. 2 and 3 illustrate perspective views of an unexploded view and an exploded view, respectively, of the adjustable bone fixation clamp 100 for securing at least two or more clamping components together, according to aspects of this disclosure. The clamp 100 includes a first clamp assembly 102, a second clamp assembly 104, a first locking member 106 (e.g. a first inner locking member), a second locking member 108 (e.g. a second inner locking member), a first sleeve 110, a second sleeve 112, a first locking assembly 114 (e.g. a first outer locking assembly), and a second locking assembly 116 (e.g. a second outer locking assembly). Each of the components of the clamp 100 are aligned along a central longitudinal axis 10 that extends from a first end 101 (e.g. distal end) to a second end 103 (e.g. proximal end) through a center of the clamp 100. It will be appreciated that fewer or more components may compose the clamp 100, and each of the components may be aligned with or offset from the longitudinal axis 10.

The first clamp assembly 102 includes a first outer vise plate 120 and a first inner vise plate 122. Similarly, the second clamp assembly 104 includes a second outer vise plate 124 and a second inner vise plate 126. The vise plates 120, 122, 124, and 126 may be made of any suitable material for clamping at least two components together, including a biocompatible material, such as metal (e.g., stainless steel, titanium, aluminum), plastic, rubber, an allow of two or more materials (e.g., titanium-aluminum-vanadium) or a composite material. It will be appreciated that any component of the clamp 100 may be made of these materials. In an aspect, the components of the clamp 100 made be made of different materials from the other components. For example, the vise plates 120, 122, 124, and 126 may be made of titanium and portions of the first and second outer locking assemblies 114 and 116 may be made of stainless steel.

The first clamp assembly 102 may be sized and configured to receive at least one fixation component such as a screw, a pin, and/or a wire. In an alternative aspect, the first clamp assembly 102 may receive at least one connector such as a rod, a pin, a bar, and/or a ring. The second clamp assembly 104 may be sized and configured to receive at least one connector such as a rod, a pin, a bar, or a ring. In another alternative aspect, the second clamp assembly 104 may be sized and configured to receive at least one fixation component such as a screw, a pin, and/or a wire.

Figure 4:
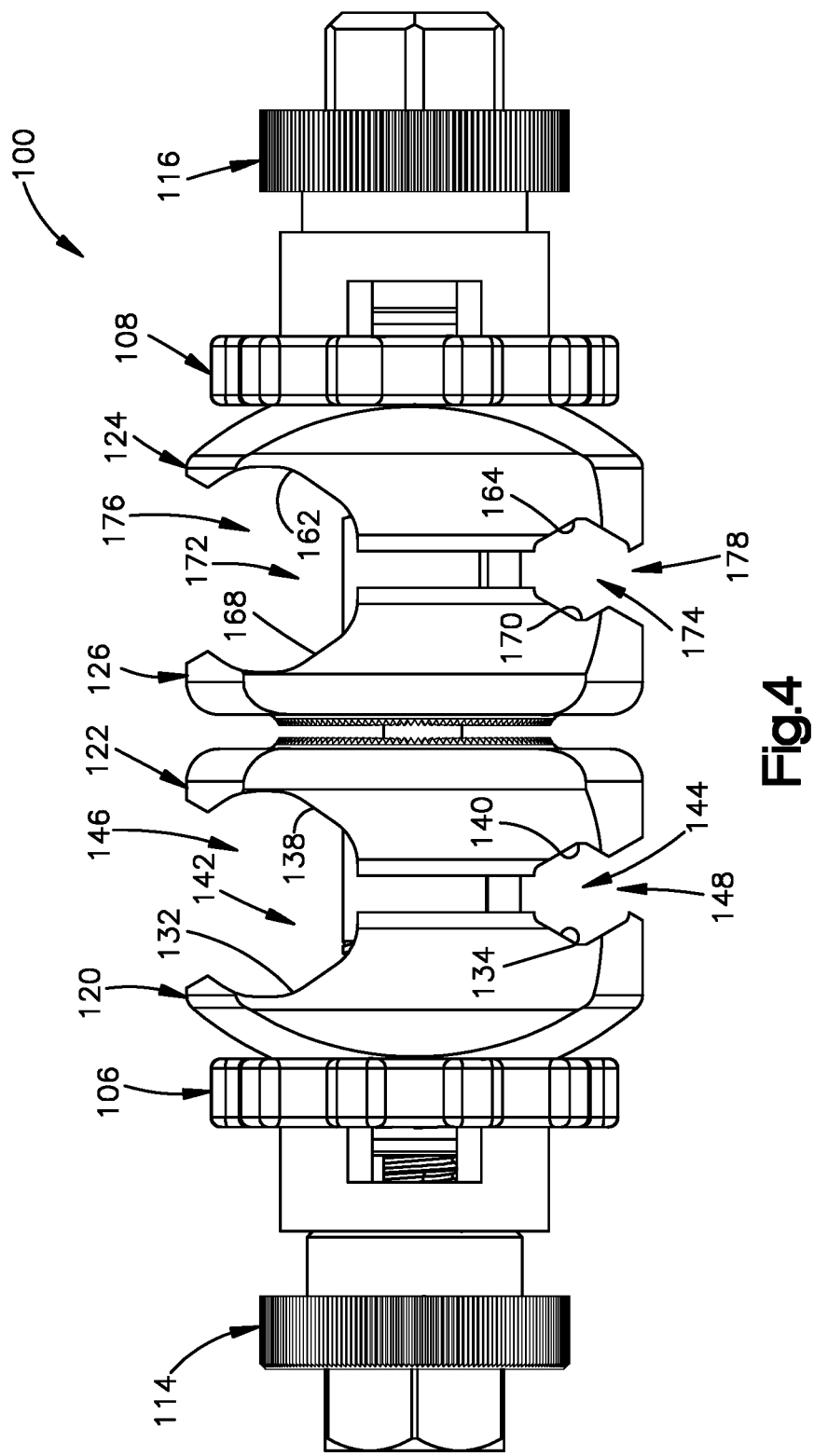
FIG. 4 illustrates a side view of the adjustable combination clamp assembly shown in FIG. 2, according to an aspect of this disclosure.

FIG. 4 illustrates a side view of the clamp 100, according to an aspect of this disclosure. FIGS. 5A and 5B illustrate a perspective view and a side view of the first outer vise plate 120, respectively, and FIGS. 6A and 6B illustrate a perspective view and a side view of the first inner vise plate 122, respectively, according to aspects of this disclosure. The first outer vise plate 120 of the first clamp assembly 102 defines a bore 130 and two recesses 132 and 134. The first inner vise plate 122 of the first clamp assembly 102 defines a bore 136 and two recesses 138 and 140. The recesses 132 and 134 of the first outer vise plate 120 correspond to the recesses 138 and 140 of the first inner vise plate 122, respectively, such that when a center of the bore 130 of the first outer vise plate 120 is aligned with a center of the bore 136 of the first inner vise plate 122 a first receiving portion 142 and a second receiving portion 144 are defined by the recesses 132 and 134 and the recesses 138 and 140, respectively. In alternative aspects, the first outer and inner vise plates 120 and 122 may have more than two recesses and consequently, may have more than two receiving portions.

The first and second receiving portions 142 and 144 may be the same size or different sizes such that the first and second receiving portions 142 and 144 may receive the same or different sized fixation components and/or connectors. The shape and/or configuration of each of the first and second receiving portions 142 and 144 may depend on the shape and/or configuration of the fixation component or connector being received within. For example, the recesses 132 and 134 of the first outer vise plate 120 and the recesses 138 and 140 of the first inner vise plate 122 may be generally V-shaped, half-rounded, u-shaped, c-shaped, polygonal, or other shape to facilitate receiving fixation components and/or connectors.

The first outer and inner vise plates 120 and 122 further define a first insertion portion 146 and a second insertion portion 148, which extend externally from outside of the first clamp assembly 102 to the respective first and second receiving portions 142 and 144. The first and second insertion portions 146 and 148 may be located at a radially outermost location of the first clamp assembly 102. The first clamp assembly 102 is configured to receive fixation components and/or connectors within the first and second receiving portions 142 and 144 through their respective first and second insertion portions 146 and 148. The insertion portions 146 and 148 may be defined by sloping surfaces of the first outer and inner vise plates 120 and 122 to assist in inserting fixation components and/or connectors.

The first outer vise plate 120 further includes a first outer contact surface 150 and a first alignment protrusion 152 extending outward from the first outer contact surface 150. In an aspect, when the first outer vise plate 120 is positioned within the clamp 100, the first alignment protrusion 152 extends outward in a direction that is substantially parallel to the longitudinal axis 10.

The first inner vise plate 122 further includes a first inner contact surface 154 and a first alignment recess 156 defined by the first inner contact surface 154. In an aspect, when the first inner vise plate 122 is positioned within the clamp 100, the first alignment recess 156 is positioned to receive the first alignment protrusion 152 within. The cooperation of the first alignment protrusion 152 and the first alignment recess 156 facilitate the alignment of the first outer vise plate 120 with the first inner vise plate 122. In an alternative aspect, the first outer vise plate 120 may include an alignment recess (not shown) and the first inner vise plate 122 may include an alignment protrusion (not shown) to facilitate alignment between the plates 120 and 122. In another alternative, the first outer and inner vise plates 120 and 122 may include multiple cooperating protrusions and recesses configured to align the plates 120 and 122.

The first inner vise plate 122 further includes a serrated portion 139 on a back surface (not labeled) of the first inner vise plate 122. The serrated portion 139 may extend circumferentially about the bore 136 and may be on an opposite side of the first inner vise plate 122 from the first inner contact surface 154.

Figure 8B:
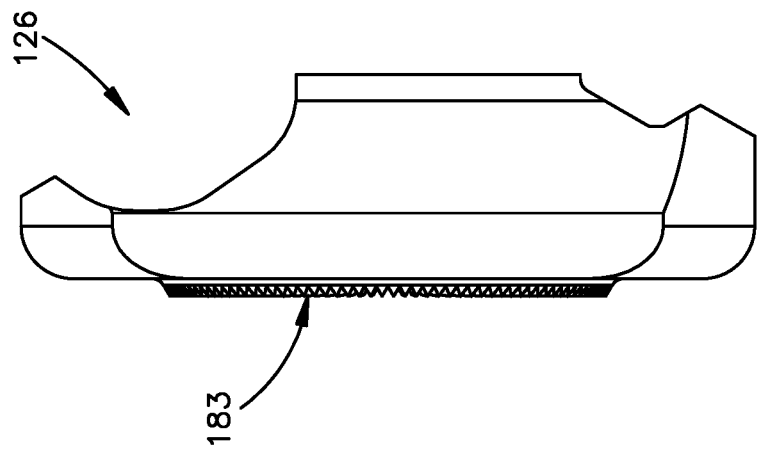
FIGS. 8A and 8B illustrate a top perspective view and a side view, respectively, of a second inner vise plate, respectively, according to aspects of this disclosure.
Figure 8A:
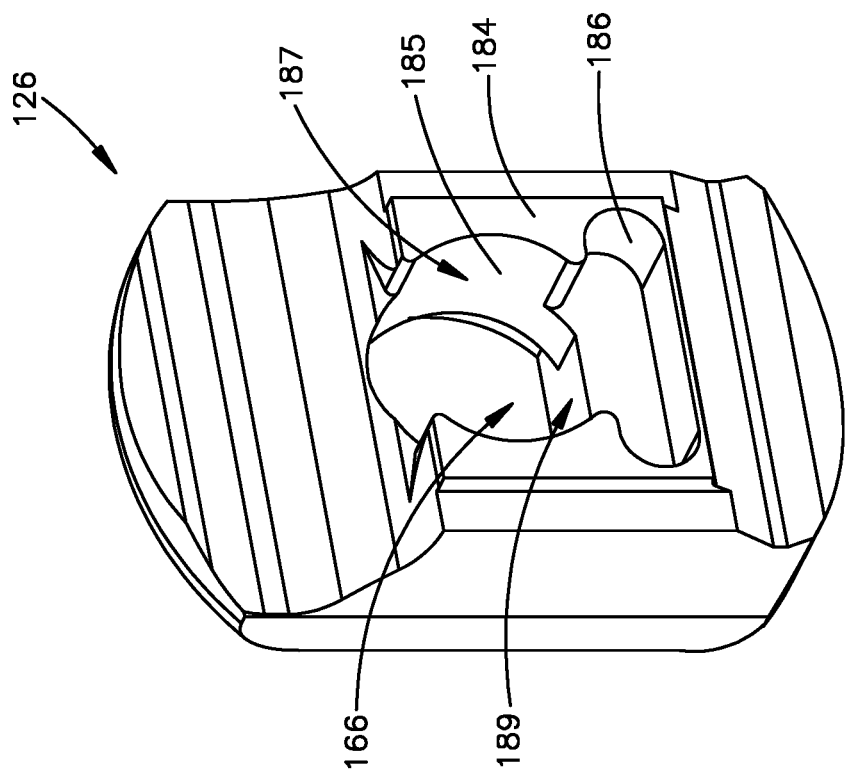

FIGS. 7A and 7B illustrate a perspective view and a side view of the second outer vise plate 124, respectively, and FIGS. 8A and 8B illustrate a perspective view and a side view of the second inner vise plate 126, respectively, according to aspects of this disclosure. The second outer vise plate 124 of the second clamp assembly 104 defines a bore 160 and two recesses 162 and 164. The second inner vise plate 126 of the second clamp assembly 104 defines a bore 166 and two recesses 168 and 170. The recesses 162 and 164 of the second outer vise plate 124 correspond to the recesses 168 and 170 of the second inner vise plate 126, respectively, such that when a center of the bore 160 of the second outer vise plate 124 is aligned with a center of the bore 166 of the second inner vise plate 126 a first receiving portion 172 and a second receiving portion 174 of the second clamp assembly 104 are defined by the recesses 162 and 164 and the recesses 168 and 170, respectively. In alternative aspects, the second outer and inner vise plates 124 and 126 may have more than two recesses and consequently, may have more than two receiving portions.

The first and second receiving portions 172 and 174 of the second clamp assembly 104 may be the same size or different sizes such that the first and second receiving portions 172 and 174 may receive the same or different sized fixation components and/or connectors. The shape and/or configuration of each of the first and second receiving portions 172 and 174 may depend on the shape and/or configuration of the fixation component or connector being received within. For example, the recesses 162 and 164 of the second outer vise plate 124 and the recesses 168 and 170 of the second inner vise plate 126 may be generally V-shaped, half-rounded, u-shaped, c-shaped, polygonal, or other shape to facilitate receiving fixation components and/or connectors.

The second outer and inner vise plates 124 and 126 further define a first insertion portion 176 and a second insertion portion 178, which extend externally from outside of the second clamp assembly 104 to the respective first and second receiving portions 172 and 174. The first and second insertion portions 176 and 178 may be located at a radially outermost location of the second clamp assembly 104. The second clamp assembly 104 is configured to receive fixation components and/or connectors within the first and second receiving portions 172 and 174 through their respective first and second insertion portions 176 and 178. The insertion portions 176 and 178 may be defined by sloping surfaces of the second outer and inner vise plates 124 and 126 to assist in inserting fixation components and/or connectors.

The first outer vise plate 124 further includes a second outer contact surface 180 and a first alignment protrusion 182 extending outward from the first outer contact surface 180. In an aspect, when the first outer vise plate 124 is positioned within the clamp 100, the first alignment protrusion 182 extends outward in a direction that is substantially parallel to the longitudinal axis 10.

The second inner vise plate 126 further includes a second inner contact surface 184 and a second alignment recess 186 defined by the second inner contact surface 184. In an aspect, when the second inner vise plate 126 is positioned within the clamp 100, the second alignment recess 186 is positioned to receive the second alignment protrusion 182 within. The cooperation of the second alignment protrusion 182 and the second alignment recess 186 facilitate the alignment of the second outer vise plate 124 with the second inner vise plate 126. In an alternative aspect, the second outer vise plate 124 may include an alignment recess (not shown) and the second inner vise plate 126 may include an alignment protrusion (not shown) to facilitate alignment between the plates 124 and 126. In another alternative, the second outer and inner vise plates 124 and 126 may include multiple cooperating protrusions and recesses configured to align the plates 124 and 126.

The second inner vise plate 126 further includes a serrated portion 183 on a back surface (not labeled) of the second inner vise plate 126. The serrated portion 183 may extend circumferentially about the bore 166 and may be on an opposite side of the second inner vise plate 126 from the second inner contact surface 184.

The second inner vise plate 126 further includes an internal surface 185 that defines the bore 166. The internal surface 185 includes a substantially cylindrical portion 187 and a planar portion 189 that both extend through the second inner vise plate 126. The configuration of the internal surface 185 corresponds to a configuration of an external surface of the second sleeve 112, as further described below.

Figure 9:
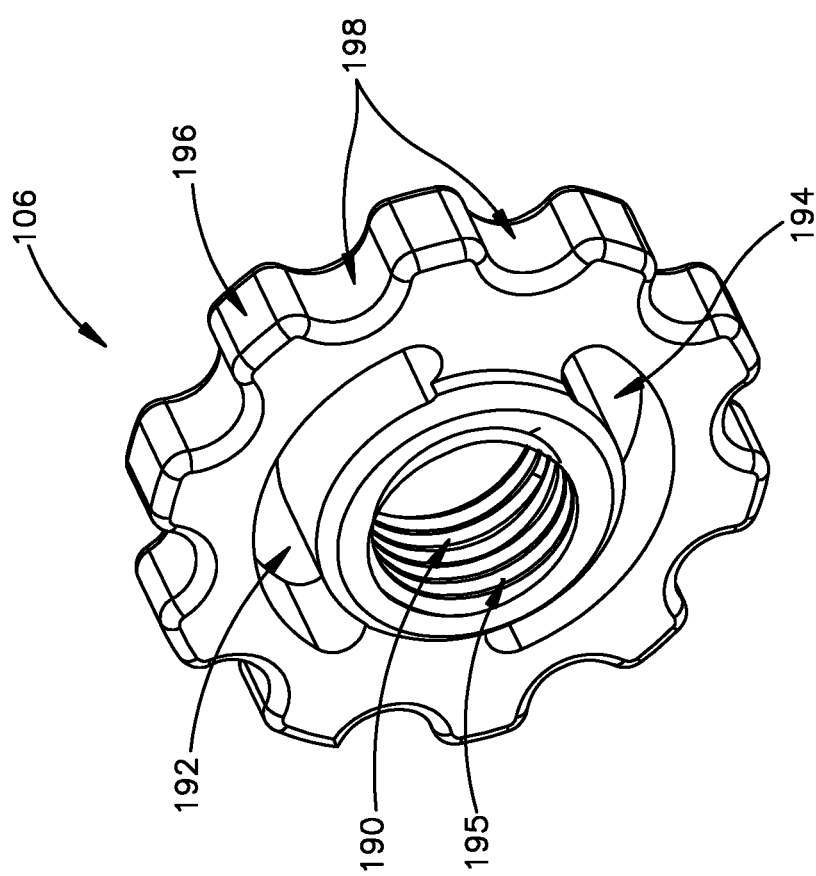
FIG. 9 illustrates a top perspective view of an inner locking member, according to an aspect of this disclosure.

FIG. 9 illustrates a perspective view of the first inner locking member 106, according to an aspect of this disclosure. The first inner locking member 106 defines a bore 190 and two locking engagement holes 192 and 194. In alternative aspects, the first inner locking member 106 may define one locking engagement hole or three or more locking engagement holes. The bore 190 and the two locking engagement holes 192 and 194 extend through the first inner locking member 106. The bore 190 defines an internal threaded region 195. The first inner locking member 106 further includes an outer circumferential surface 196 that defines a plurality of ridges 198. In an aspect, the outer circumferential surface 196 may define one ridge or other features configured to facilitate rotation of the first inner locking member 106 in a circumferential direction by a user. It will be appreciated that the second inner locking member 108 may be configured substantially similarly as the first inner locking member 106.

FIGS. 10A, 10B, and 10C illustrate a front perspective view, a back perspective view, and a front view of the first sleeve 110, according to aspects of this disclosure. The first inner locking member 106 and the first sleeve 110 may compose a first inner locking sub-assembly (not labeled). The first sleeve 110 includes an external surface 200, an opposed internal surface 202, an outer end 201, and an inner end 203. The external and internal surfaces 200 and 202 extend from the outer end 201 to the inner end 203. The internal surface 202 defines a bore 204 that extends through the first sleeve 110. The external surface 200 defines a threaded portion 206 and a non-threaded portion 208. The threaded portion 206 extends from non-threaded portion 208 toward the outer end 201, and the unthreaded portion 208 extends from the threaded portion 206 toward the inner end 203. The first sleeve 110 further includes a first support shelf 214 positioned at the inner end 203.

The internal surface 202 of the first sleeve 110 defines a substantially cylindrical portion 210 that extends about a central axis, and a planar portion 212. The cylindrical portion 210 and the planar portion 212 extend from the outer end 201 to the inner end 203 of the first sleeve 110 to define the bore 204. The planar portion 212 may extend in a direction that is substantially parallel to the central axis of the first sleeve 110. In alternative aspects, the internal surface 202 of the first sleeve 110 may define other shapes, including, for example, elliptical, square, rectangular, hexagonal, or other polygon. The configuration of the internal surface 202 corresponds to a configuration of the second outer locking assembly 116, as further described below.

FIGS. 11A, 11B, and 11C illustrate a front perspective view, a back perspective view, and a front view of the second sleeve 112, according to aspects of this disclosure. The second inner locking member 108 and the second sleeve 112 may compose a second inner locking sub-assembly (not labeled). The second sleeve 112 includes an external surface 220, an opposed internal surface 222, an outer end 221, and an inner end 223. The external and internal surfaces 220 and 222 extend from the outer end 221 to the inner end 223. The internal surface 222 defines a bore 224 that extends through the second sleeve 112. The external surface 220 defines a threaded portion 226 and a non-threaded portion 228. The threaded portion 226 extends from unthreaded portion 228 toward the outer end 221, and the unthreaded portion 228 extends from the threaded portion 226 toward the inner end 223. The second sleeve 112 further includes a second support shelf 234 positioned at the inner end 203.

The external surface 220 of the second sleeve 112 further defines a substantially cylindrical portion 230 that extends about a central axis that extends through a center of the bore 224, and a planar portion 232. The cylindrical portion 230 extends from the second support shelf 234 to the outer end 221. The planar portion 232 extends along a length of the second sleeve 112 from the outer end 221 to the inner end 223. At least a portion of the planar portion 232 is defined by the second support shelf 234. In alternative aspects, the external surface 220 of the second sleeve 112 may have other shapes and/or configurations, including, for example, elliptical, square, rectangular, hexagonal, or other polygon. The configuration of the external surface 220 corresponds to a configuration of the internal surface 185 of the second inner vise plate 126, such that when the second sleeve 112 is positioned within the bore 166 of the second inner vise plate 126, the second sleeve 112 and the second inner vise plate 126 are substantially prevented from rotational movement relative to each other.

Figure 13:
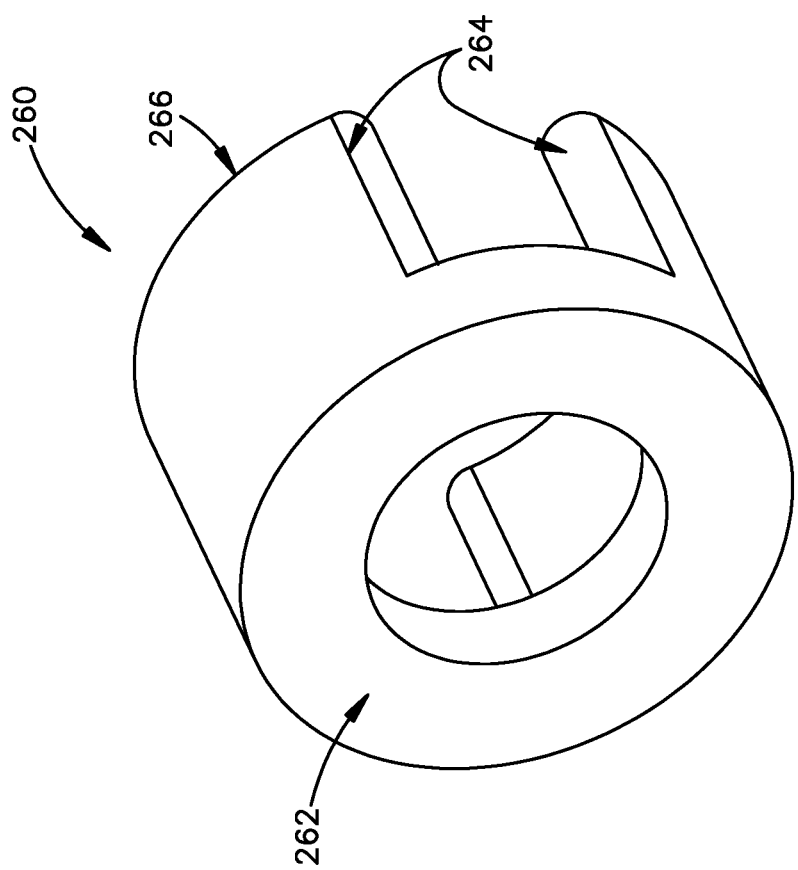
FIG. 13 illustrates a top perspective view of a first outer locking member, according to an aspect of this disclosure.
Figure 12:
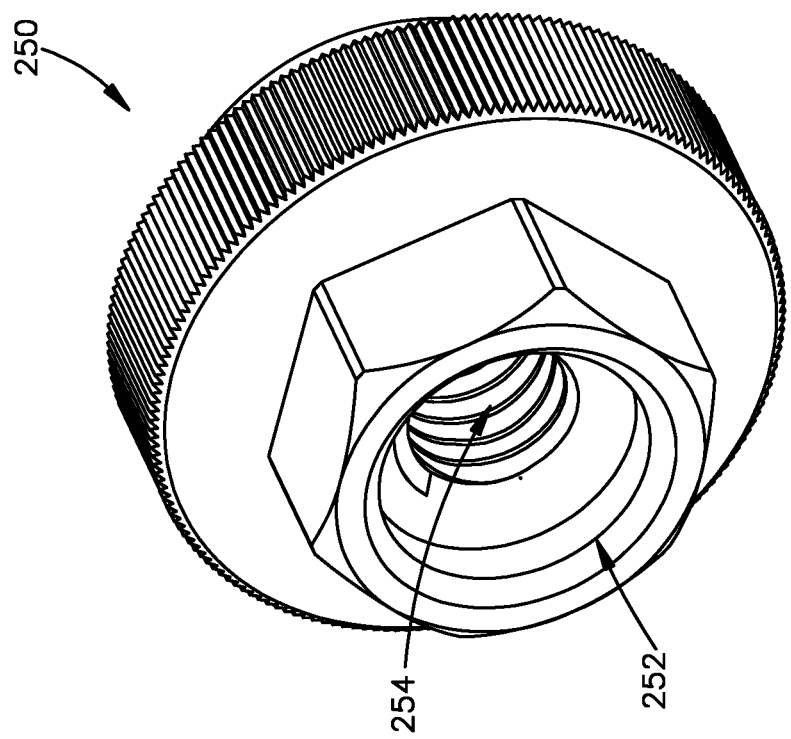
FIG. 12 illustrates a top perspective view of a first end component, according to an aspect of this disclosure.

The first external locking assembly 114 includes a first end component 250 (e.g. a nut) and a first contact member 260 (e.g. a first outer locking member). FIGS. 12 and 13 illustrate perspective views of the first end component 250 and the first outer locking member 260, respectively, according to aspects of this disclosure. The first end component 250 defines a bore 252 extending therethrough and an internal threaded region 254. The first end component 250 may also include other features for rotation as well as hex flats to facilitate rotation of the component by, for example, a wrench. The first outer locking member 260 includes a base 262 and a pair of arms 264 that extend out from the base 262 toward an inner end 266 of the first outer locking member 260. The pair of arms 264 are positioned radially outward from the bore 252. In alternative aspects, the pair of arms 264 may include a single arm or three or more arms. In an aspect, the total number of arms corresponds to the number of locking engagement holes 192 and 194 of the first inner locking member 106. For example, if the first inner locking member 106 includes four locking engagement holes, then the first outer locking member 260 may include two pairs of arms 264.

The second outer locking assembly 116 includes a second end component 270 and a second contact member 290 (e.g. a second outer locking member). FIGS. 14 and 15 illustrate perspective views of the second end component 270 and the second outer locking member 290, respectively, according to aspects of this disclosure. The second outer locking member 290 includes a base 292 and a pair of arms 294 that extend out from the base 292 toward an inner end 296 of the second outer locking member 290. In an aspect, the second outer locking member 290 may be configured substantially similarly as the first outer locking member 260.

The second end component 270 includes a shaft 272 and a head component 274. The head component 274 is positioned at a second end 273 of the shaft 272. The shaft 272 extends from the head component 274 at the second end 273 to a first end 271 of the shaft 272. The head component 274 may be integrally formed with the shaft 272 forming a single unitary component. Alternatively, the head component 274 may be a separate component that is secured to the second end 273 of the shaft by a threaded connection, weld, glue, or other adhesive connection known in the art. If the head component 274 includes a threaded connection, the component 274 may operate substantially similarly to the first end component 250. The head component 274 may also include other features for rotation as well as hex flats to facilitate rotation of the component 274 by, for example, a wrench.

The shaft 272 has an external surface 276 that defines a substantially cylindrical portion 278 that extends from the first end 271 to the second end 273, and a planar portion 280. The planar portion 280 extends along a length of the shaft 272 from the first end 271 toward the second end 273. In an aspect, the planar portion 280 extends from the first end 271 to a location between the first end 271 and the second end 273 forming a shaft shoulder 282 on the external surface 276. The external surface 276 of the shaft 270 further defines a threaded portion 284 and a non-threaded portion 286. The threaded portion 284 extends from the first end 271 to the unthreaded portion 286, and the unthreaded portion 286 extends from the threaded portion 284 toward the second end 273. In an aspect, the planar portion 280 may extend along portions of both the threaded portion 286 and the non-threaded portion 286 of the shaft 272.

Figure 16:
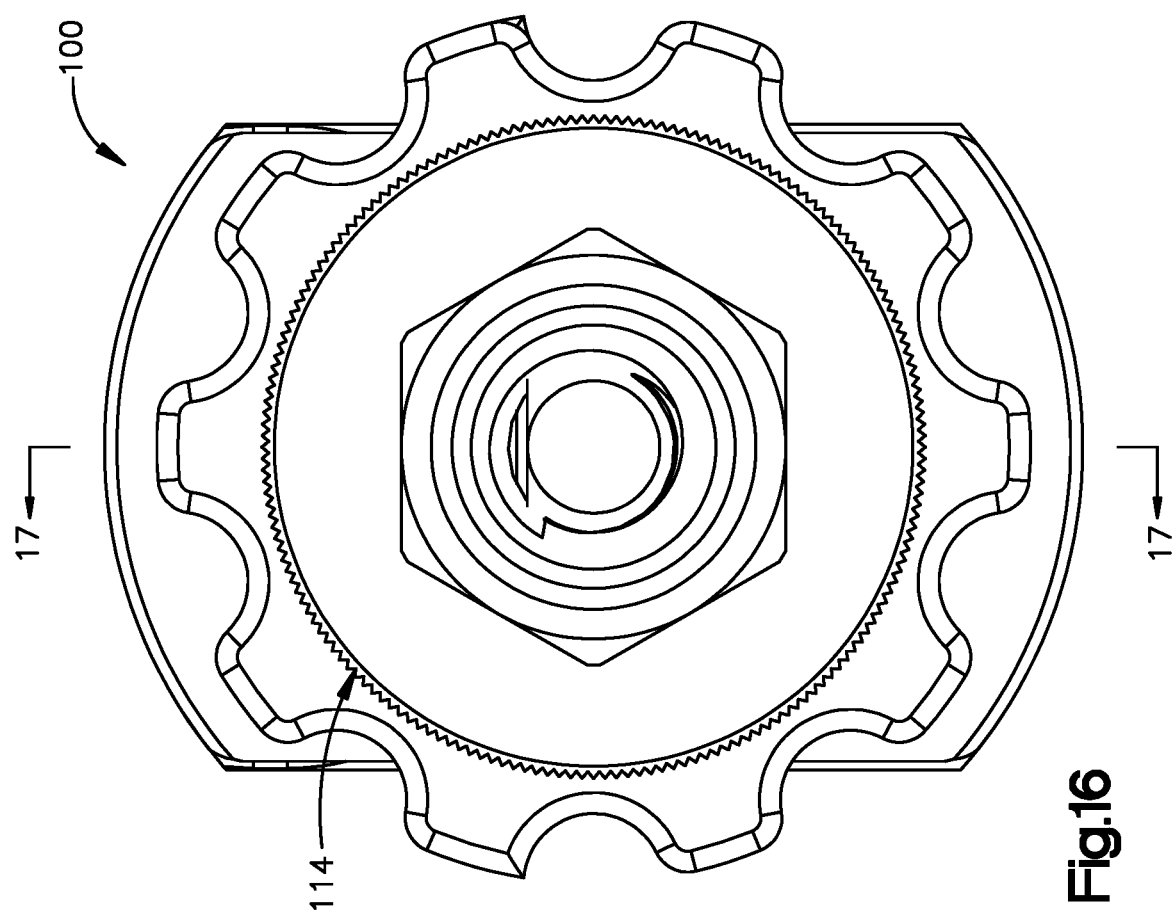
FIG. 16 illustrates a side view of the clamp assembly illustrated in FIG. 2, according to an aspect of this disclosure.
Figure 17:
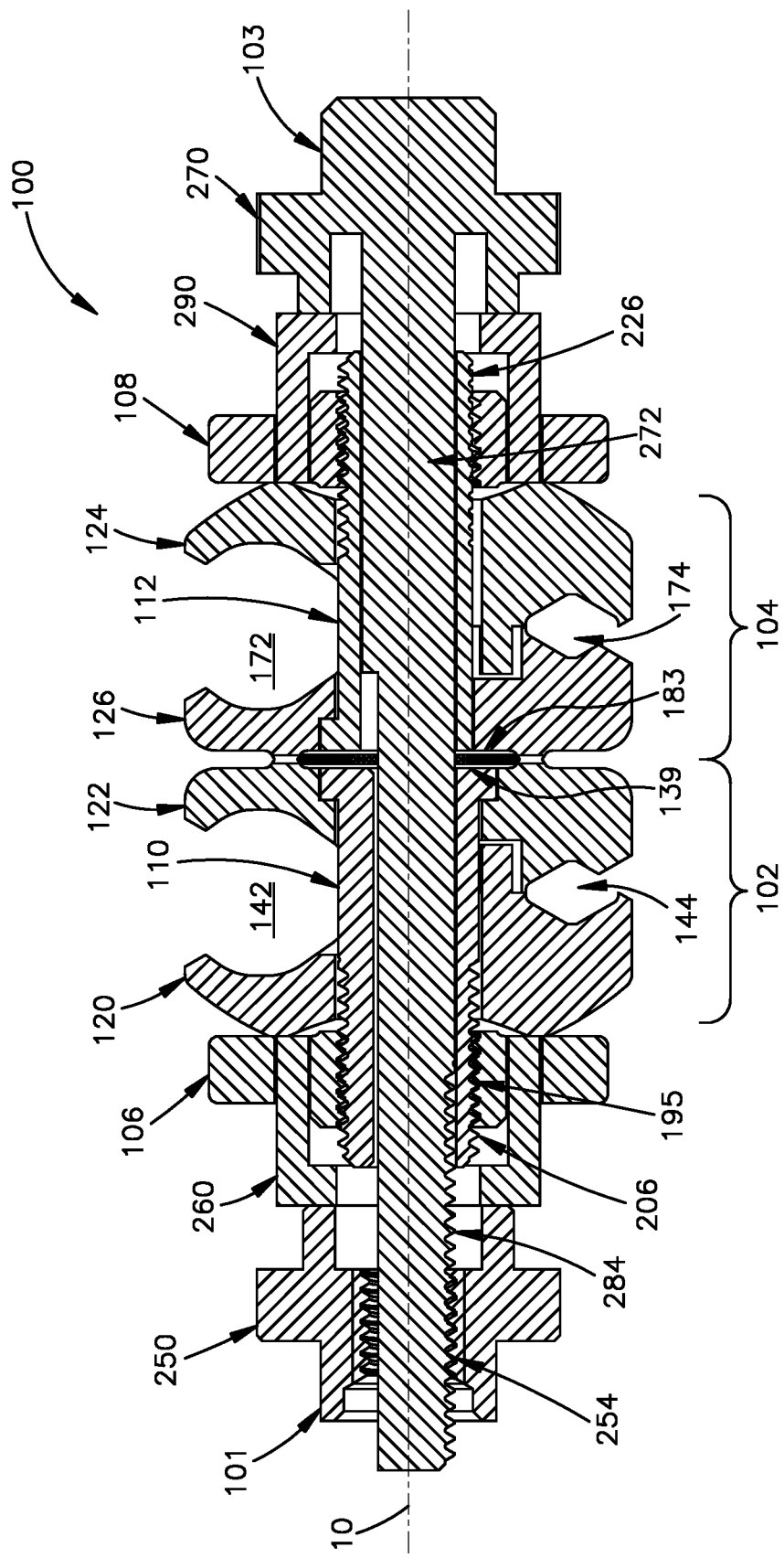
FIG. 17 illustrates a cross-sectional view of the clamp assembly in a closed configuration taken along line 17-17 of FIG. 16, according to an aspect of this disclosure.

FIG. 16 illustrates a side view of the assembled configuration of the clamp 100 illustrated in FIGS. 2 and 4. FIG. 17 illustrates a cross-sectional view of the assembled configuration of the clamp 100 taken along line 17-17 of FIG. 16. The clamp 100 is assembled by positioning each of the assemblies and/or components onto the shaft 272. The second end 103 of the clamp 100 is defined by the second end component 270. The second outer locking member 290 is positioned on the shaft 272 such that the base 292 contacts the head component 274 of the second end component 270. The second outer locking member 290 is aligned such that the pair of arms 294 extend from the base 292 of the member 290 toward the first end 101 of the clamp 100.

After the second outer locking member 290 is positioned on the shaft 272, the second inner locking sub-assembly, including the second inner locking member 108 and the second sleeve 112, and the second outer and inner vise plates 124 and 126 are positioned on the shaft 272. Prior to positioning the second inner locking sub-assembly onto the shaft 272, the second outer and inner vise plates 124 and 126 may be positioned on the external surface 220 of the second sleeve 112, such that the cylindrical portion 230 of the second sleeve 112 extends through the bores 160 and 166 of the second outer and inner vise plates 124 and 126, respectively. A back surface of the inner vise plate 126 may abut against the second support shelf 234 of the second sleeve 112. The second outer and inner vise plates 124 and 126 are aligned on the external surface 220 such that the first alignment protrusion 182 is positioned within the second alignment recess 186 of the inner vise plate 126. The interface between the second outer and inner vise plates 124 and 126 enables linear movement between the second outer and inner vise plates 124 and 126, while substantially preventing rotational movement of the outer vise plate 124 relative to the second inner vise plate 126 about the external surface 220 of the second sleeve 112. Further, the planar portion 189 of the second inner vise plate 126 aligns with the planar portion 232 of the second sleeve 112 such that rotation of the second inner vise plate 126 relative to the second sleeve 112 is substantially prevented.

After the second outer and inner vise plates 124 and 126 are positioned on the second sleeve 112, the second inner locking member 108 is threadedly connected to the threaded portion 226 of the second sleeve 112. The second support shelf 234 of the second sleeve 112 and the second inner locking member 108 retain the second outer and inner vise plates 124 and 126 on the second sleeve 112.

After the second inner locking member 108 is threadedly connected to the threaded portion 226 of the second sleeve 112, the second sleeve 112 with the second outer and inner vise plates 124 and 126 positioned thereon is positioned onto the shaft 272 of the second end component 270. The shaft 272 extends through the bore 224 of the second sleeve 112. The second sleeve 112 is rotatable about the external surface 276 of the shaft 272. The second inner locking member 108, which is threadedly connected to the second sleeve 112, aligns with the second outer locking member 290 such that the arms 294 of the second outer locking member 290 are positioned within engagement holes of the second inner locking member 108. The connection between the second inner locking member 108 and the second outer locking member 290 substantially prevents rotational movement of the second outer locking member 290 relative to the second inner locking member 108 while allowing linear movement of the second outer locking member 290 relative to the second inner locking member 108.

After the second inner locking sub-assembly and the second outer and inner vise plates 124 and 126 are positioned on the shaft 272, the first inner locking sub-assembly, including the first inner locking member 106 and the first sleeve 110, and the first outer and inner vise plates 120 and 122 are positioned on the shaft 272. Prior to positioning the first inner locking sub-assembly onto the shaft 272, the first outer and inner vise plates 120 and 122 may be positioned on the external surface 200 of the first sleeve 110, such that the first sleeve 110 extends through the bores 130 and 136 of the first outer and inner vise plates 120 and 122, respectively. A back surface of the inner vise plate 122 may abut against the first support shelf 214 of the first sleeve 110. The first outer and inner vise plates 120 and 122 are aligned on the external surface 200 such that the first alignment protrusion 152 is positioned within the first alignment recess 156 of the first inner vise plate 122. The interface between the first outer and inner vise plates 120 and 122 enables linear movement between the first outer and inner vise plates 120 and 122, while substantially preventing rotational movement of the first outer vise plate 120 relative to the first inner vise plate 122 about the external surface 200 of the first sleeve 110.

After the first outer and inner vise plates 120 and 122 are positioned on the first sleeve 110, the internal threaded region 195 of the first inner locking member 106 is threadedly connected to the threaded portion 206 of the first sleeve 110. The first support shelf 214 of the first sleeve 110 and the first inner locking member 106 retain the first outer and inner vise plates 120 and 122 on the first sleeve 110.

After the first inner locking member 106 is threadedly connected to the threaded portion 206 of the first sleeve 110, the first sleeve 110 with the first outer and inner vise plates 120 and 122 positioned thereon is positioned onto the shaft 272 of the second end component 270. The shaft 272 extends through the bore 204 of the first sleeve 110. The planar portion 212 of the internal surface 202 of the first sleeve 110 aligns with the planar portion 280 of the external surface 276 of the shaft 272 such that rotation of the first sleeve 110 relative to the shaft 272 is substantially prevented.

After the first inner locking sub-assembly and the first outer and inner vise plates 120 and 122 are positioned on the shaft 272, the first outer locking member 260 is positioned on the shaft 272. The first outer locking member 260 aligns with the first inner locking member 106 such that the arms 264 of the first outer locking member 260 are positioned within respective engagement holes 192 and 194 of the first inner locking member 106. The connection between the first inner locking member 106 and the first outer locking member 260 substantially prevents rotational movement of the first outer locking member 260 relative to the first inner locking member 106 while allowing linear movement of the first outer locking member 260 relative to the first inner locking member 106.

After the first outer locking member 260 is positioned on the shaft 272, the first end component 250 is positioned on the shaft 272. The internal threaded region 254 of the first end component 250 engages the threaded portion 284 of the shaft 272. The first end component 250 may abut against the base 262 of the first outer locking member 260. In an aspect, to prevent the first outer locking member 260 from separating from the shaft 272 upon rotation, the threaded portion 284 of the shaft 272 may be deformed at the first end 271.

It will be appreciated that other components may be included in the clamp 100. For example, a biasing member (not shown) may be positioned on the shaft 272 between the first inner vise plate 122 and the second inner vise plate 126. The biasing member may include, for example, a coil spring, a wave spring, a bellows spring, a rubber element, a flexible plastic element, or other similar spring known in the art. The biasing member may bias the first inner vise plate 122 away from the second inner vise plate 126, which biases the first inner vise plate 122 toward the first outer vise plate 120 and biases the second inner vise plate 126 toward the second outer vise plate 124. In an alternative aspect, a biasing member could be positioned between the first outer and inner vise plates 120 and 122 and/or between the second outer and inner vise plates 124 and 126. In another alternative aspect, biasing members could be positioned between all the vise plates or between some of the vise plates. The biasing members may be configured to form a snap-fit type connection between a fixation component and/or a connector and the first and second clamp assemblies 102 and 104 when the a fixation component and/or the connector is inserted through any of the first and second insertion portions 146 and 148 of the first clamp assembly 102 or inserted into any of the first and second insertion portions 176 and 178 of the second clamp assembly 104. For example, after a fixation component is inserted through the sloping surfaces of the first insertion portion 146 and into the receiving portion 142 of the first clamp assembly 102 the first outer and inner vise plates 120 and 122 may snap together either contacting each other or both contacting the fixation component.

Figure 18:
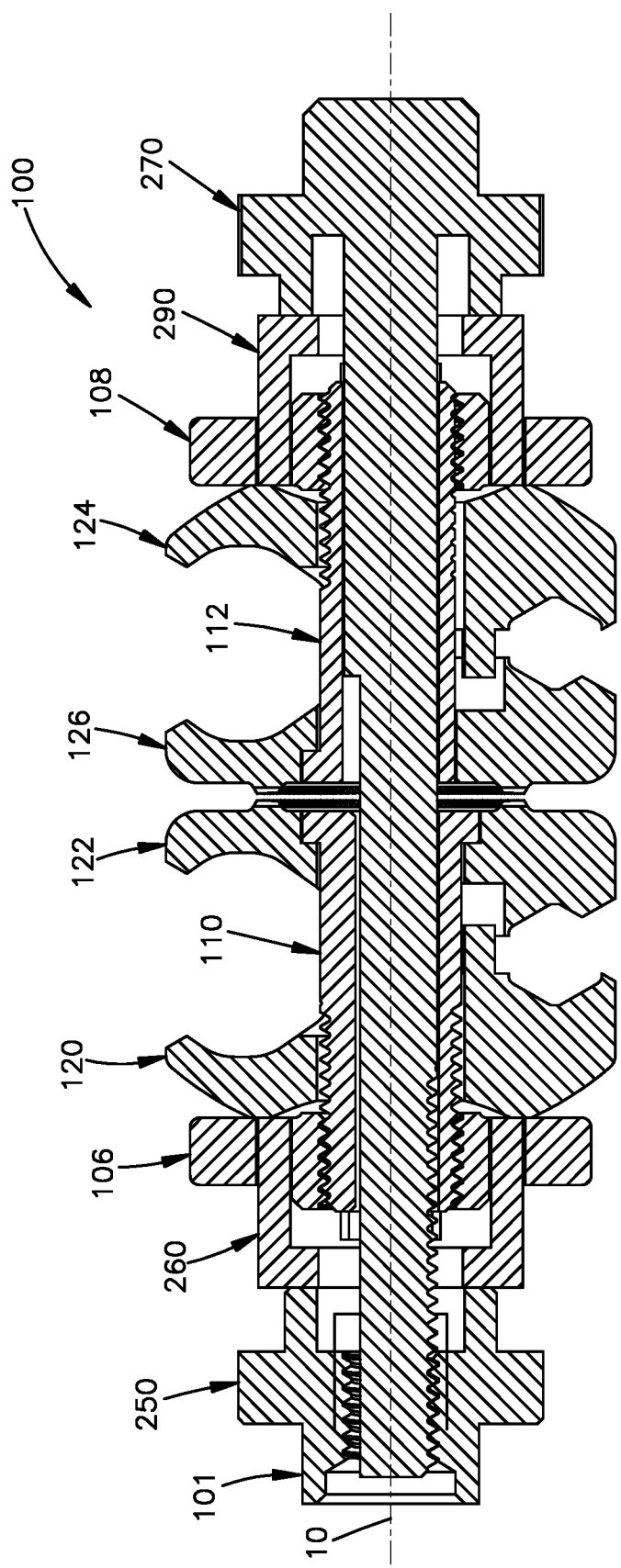
FIG. 18 illustrates a cross-sectional view of a clamp assembly in an open configuration, according to an aspect of this disclosure.

FIG. 17 illustrates the cross-sectional view of the clamp 100 in a closed configuration, and FIG. 18 illustrates a cross-sectional view of the clamp 100 in an open configuration, according to aspects of this disclosure. In the open configuration of the clamp 100, both of the first clamp assembly 102 and the second clamp assembly 104 are in their respective open configurations, as described in further detail below. Similarly, in the closed configuration of the clamp 100, both of the first clamp assembly 102 and the second clamp assembly 104 are in their respective closed configurations, as described in further detail below. In the closed configuration illustrated in FIG. 17, the first and second inner locking members 106 and 108 may be utilized prior to the outer locking assemblies 114 and 116.

The first inner locking member 106 is configured to transition between a locked position and an unlocked position by rotating about the threaded portion 206 of the first sleeve 110. In the locked position, the first inner locking member 106 abuts against the first outer vise plate 120 substantially preventing the first outer vise plate 120 from linear or rotational movement along the first sleeve 110 between the first locking member 106 and the first inner vise plate 122. In the locked position of the first locking member 106, the first outer vise plate 120 may be in contact with a fixation component and/or a connector positioned within either the first and/or second receiving portions 142 and 144, thereby retaining the fixation component and/or connector within and substantially preventing movement of the first outer vise plate 120 along the first sleeve 110. Alternatively, in the locked position of the first locking member 106, the first outer contact surface 150 of the first outer vise plate 120 may be in contact with the first inner contact surface 154 of the first inner vise plate 122, thereby substantially preventing movement of the first outer vise plate 120 along the first sleeve 120. In the locked position of the first locking member 106, the first clamp assembly 102 is in a closed configuration. In the closed configuration, the first outer and inner vise plates 120 and 122 are substantially linearly and rotationally fixed relative to one another.

In the unlocked position of the first locking member 106, the first locking member 106 does not substantially prevent linear or rotational movement of the first outer vise plate 120 about the first sleeve 110. In the unlocked position, the first clamp assembly 102 may be in an open configuration. In the open configuration, the first outer and inner vise plates 120 and 122 are substantially free to move relative to each other.

Similar to the first inner locking member 106, the second inner locking member 108 is configured to transition between a locked position and an unlocked position by rotating about the threaded portion 226 of the second sleeve 112. In the locked position, the second inner locking member 108 abuts against the second outer vise plate 124 substantially preventing the second outer vise plate 124 from linear movement along the second sleeve 112 between the second locking member 108 and the second inner vise plate 126. In the locked position of the second locking member 108, the second outer vise plate 124 may be in contact with a fixation component and/or a connector positioned within either the first and/or second receiving portions 172 and 174, thereby retaining the fixation component and/or connector within and substantially preventing movement of the second outer vise plate 124 along the second sleeve 112. Alternatively, in the locked position of the second locking member 108, the second outer contact surface 180 (see FIG. 7A) of the second outer vise plate 124 may be in contact with the second inner contact surface 184 (see FIG. 8A) of the second inner vise plate 126, thereby substantially preventing movement of the second outer vise plate 124 along the first sleeve 120. In the locked position of the second locking member 108, the second clamp assembly 104 is in a closed configuration. In the closed configuration, the second outer and inner vise plates 124 and 126 are substantially linearly and rotationally fixed relative to one another.

In the unlocked position of the second locking member 108, the second locking member 108 does not substantially prevent linear movement of the second outer vise plate 124 about the second sleeve 120. In the unlocked position, the second clamp assembly 104 may be in an open configuration. In the open configuration, the second outer and inner vise plates 124 and 126 are substantially free to move relative to each other.

The first and second outer locking assemblies 114 and 116 are together configured to transition between a locked position and an unlocked position by rotating the first end component 250 about the on the threaded portion 284 of the shaft 272 of the second end component 270. In this regard, the first and second outer locking assemblies 114 and 116 may be referred to as "the outer locking assembly." In the locked position, the first end component 250 abuts against the first outer locking member 260, which abuts against the first outer vise plate 120; and the second end component 270 abuts against the second outer locking member 290, which abuts against the second outer vise plate 124. In the locked position of the first and second outer locking assemblies 114 and 116, the first outer vise plate 120 may be in contact with a fixation component and/or a connector positioned within either the first and/or second receiving portions 142 and 144, and the second outer vise plate 124 may be in contact with a fixation component and/or a connector positioned within either the first and/or second receiving portions 172 and 174. The fixation components and/or connectors within the respective first and/or second receiving portions 142 and 144 and the first and/or second receiving portions 172 and 174 are retained within the respective portions, and the movement of each of the first and second outer vise plates 120 and 124 is substantially prevented along the respective first and second sleeve 110 and 112. Alternatively, in the locked position of the first and second outer locking assemblies 114 and 116, the first outer contact surface 150 (see FIG. 5A) of the first outer vise plate 120 may be in contact with the first inner contact surface 154 (see FIG. 6A) of the first inner vise plate 122 substantially preventing movement of the first outer vise plate 120 along the first sleeve 120, and the second outer contact surface 180 (see FIG. 7A) of the second outer vise plate 124 may be in contact with the second inner contact surface 184 (see FIG. 8A) of the second inner vise plate 126 substantially preventing movement of the second outer vise plate 124 along the first sleeve 120.

In the locked position of the first and second outer locking assemblies 114 and 116, both of the first clamp assembly 102 and the second clamp assembly 104 are in their respective closed configurations regardless of the position of either of the first and second inner locking members 106 and 108. For example, if the first and second outer locking assemblies 114 and 116 are in the locked position and the first inner locking member 106 is in the unlocked position, the first clamp assembly 102 is in the closed configuration. Likewise, if the first and second outer locking assemblies 114 and 116 are in the locked position and the second inner locking member 108 is in the unlocked position, the second clamp assembly 104 is in the closed configuration. In the locked position of the first and second outer locking assemblies 114 and 116, the outer locking assemblies 114 and 116 substantially prevents both the first outer vise plate 120 from moving relative to the first inner vise plate 122 along the longitudinal axis 10 and rotationally about the axis 10 and the second outer vise plate 124 from moving relative to the second inner vise plate 126 along the longitudinal axis 10 and rotationally about the axis 10.

Additionally, in the locked position of the first and second outer locking assemblies 114 and 116, the back surface of the first inner vise plate 122 abuts against the back surface of the second inner vise plate 126 so that the serrated portion 139 of the first inner vise plate 122 interfaces with the serrated portion 183 of the second inner vise plate 126. The interface between the serrated portions 139 and 183 substantially prevents rotation of the first clamp assembly 102 relative to the second clamp assembly 104. It will be appreciated that the back surfaces of the first inner vise plate 122 and the second inner vise plate 126 may include alternative locking features configured to substantially prevent rotation between the two plates 122 and 126.

In the unlocked position of the first and second outer locking assemblies 114 and 116, the outer locking assemblies 114 and 116 do not substantially prevent linear or rotational movement of the first outer vise plate 120 about the first sleeve 110 or substantially prevent linear movement of the second outer vise plate 124 about the second sleeve 112. Additionally, the back surfaces of the first inner vise plate 122 and the second inner vise plate 126 may not abut. For example, a biasing member may be positioned between the back surface of the first inner vise plate 122 and the back surface of the second inner vise plate 126 biasing the plates 122 and 126 apart. With the first inner vise plate 122 spaced apart from the second inner vise plate 126, serrated portions 139 and 183 of the respective first and second inner vise plates 122 and 126 are not in contact, allowing the first clamp assembly 102 to rotate relative to the second clamp assembly 104 about the shaft 272 of the second end component 270.

Figure 19A:
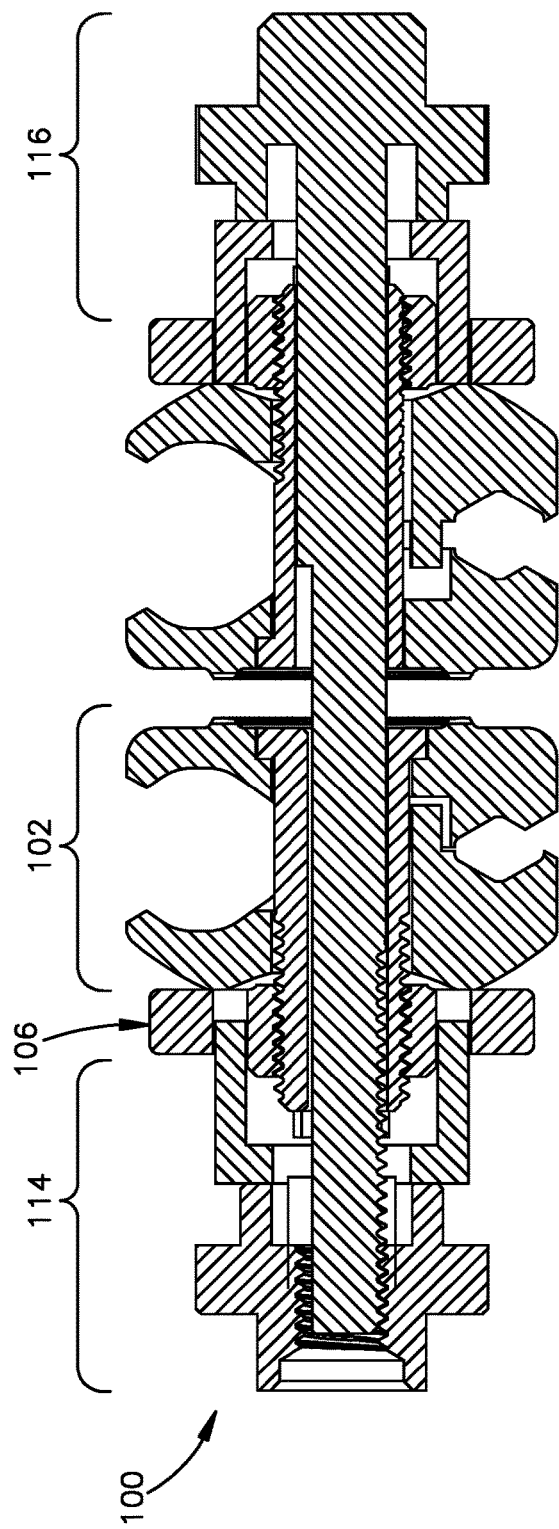
FIG. 19A illustrates a cross-sectional view of a clamp assembly with a first locking member in a locked position, according to an aspect of this disclosure.
Figure 19B:
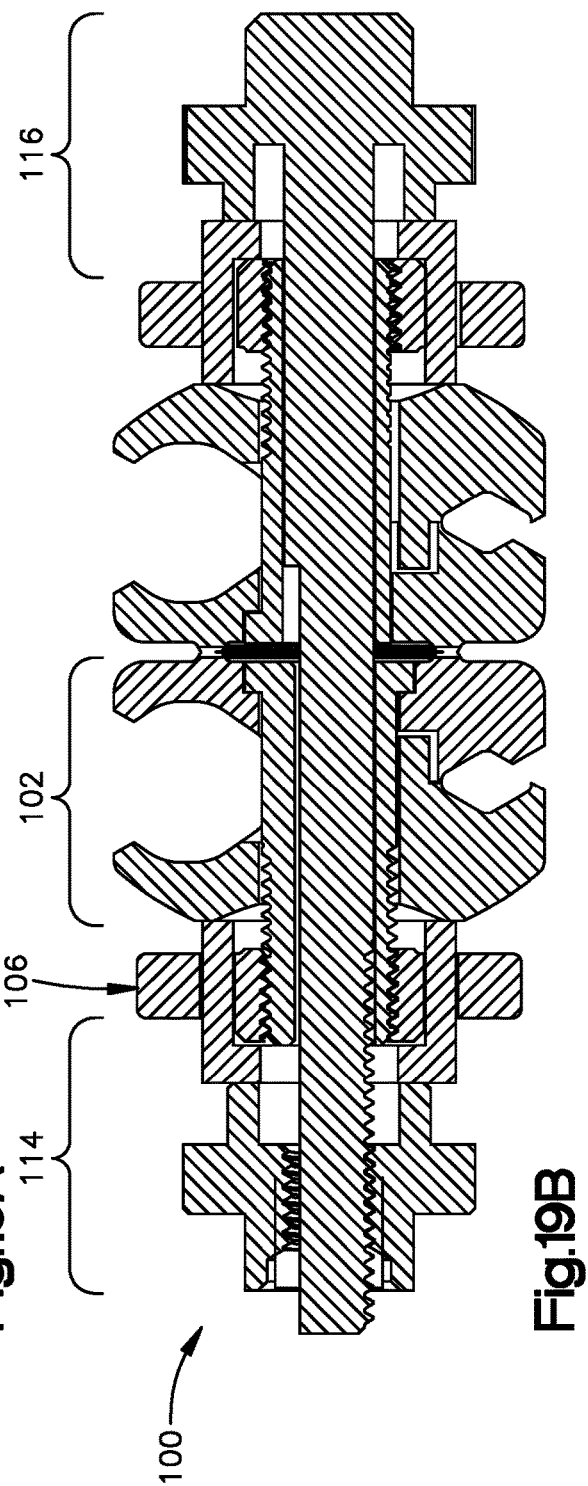
FIG. 19B illustrates a cross-sectional view of a clamp assembly with an outer locking assembly in a locked position, according to an aspect of this disclosure.

In the unlocked position of the first and second outer locking assemblies 114 and 116, the first clamp assembly 102 and the second clamp assembly 104 may be in their respective open configurations. For example, if the first and second outer locking assemblies 114 and 116 are in the unlocked position and the first inner locking member 106 is in the unlocked position, the first clamp assembly 102 is in the open configuration. However, as illustrated in FIG. 19A, if the first and second outer locking assemblies 114 and 116 are in the unlocked position and first inner locking member 106 is in the locked position, the first clamp assembly 102 is in the closed configuration. Likewise, as illustrated in FIG. 19B, if the first and second outer locking assemblies 114 and 116 are in the locked position and the first inner locking member 106 is in the unlocked position, the first clamp assembly 102 is in the closed configuration. It will be appreciated that the open and closed configuration of the second clamp assembly 104 may be controlled substantially similarly to the open and closed configuration of the first clamp assembly 102.

In the unlocked position of the first and second outer locking assemblies 114 and 116, the first and second inner locking members 106 and 108 are substantially free to transition the first and second clamp assemblies 102 and 104, respectively, between their open and closed configurations. In the locked position of the first and second outer locking assemblies 114 and 116, the first and second clamp assemblies 102 and 104 remain in their closed configuration regardless of the positions of either of the first and second inner locking members 106 and 108.

When the first and second outer locking assemblies 114 and 116 are in the unlocked position, and both of the first and second inner locking members 106 and 108 are in their respective locked position, the first and second clamp assemblies 102 and 104 are in their respective closed configurations. In this configuration, which is illustrated in FIG. 20, the first clamp assembly 102 is substantially free to rotate relative to the second clamp assembly 104. For example, the serrated portion 139 of the first inner vise plate 122 is spaced apart from the serrated portion 183 of the second inner vise plate 126, the first clamp assembly 102 is rotationally fixed to the shaft 272 of the second end component 270 by the first sleeve 110, and the second clamp assembly 104 is substantially free to rotated about the shaft 272.

During use of the clamp 100, the first and second outer locking assemblies 114 and 116 and the first and second inner locking members 106 and 108 may be in their respective unlocked positions. A first fixation component and/or connector may be positioned within either or both of the first and second receiving portions 142 and 144 of the first clamp assembly 102. The first clamp assembly 102 may be transitioned from the open configuration to the closed configuration by transitioning the first inner locking member 106 to the locked position. A second fixation component and/or connector may be positioned within either or both of the first and second receiving portions 172 and 174 of the second clamp assembly 104. The second clamp assembly 104 may be transitioned from the open configuration to the closed configuration by transitioning the second inner locking member 108 to the locked position. After the first and second fixation components and/or connectors are secured within their respective first and second clamp assemblies 102 and 104, the first and second clamp assemblies 102 and 104 may be rotated relative to one another to a desired position. Once the first and second clamp assemblies 102 and 104 are in their desired position, the first and second outer locking assemblies 114 and 116 may be transitioned to the locked position, thereby substantially rotationally locking the first clamp assembly 102 with the second clamp assembly 104.

To remove or adjust the clamp 100, each of the first and second clamp assemblies 102 and 104 may be controlled individually. For example, the first and second outer locking assemblies 114 and 116 may be transitioned to the unlocked position, and to remove or adjust the first fixation component and/or connector the first inner locking member 106 may be transitioned to the unlocked position. With both the first and second outer locking assemblies 114 and 116 and the first inner locking member 106 in the unlocked positions, the first clamp assembly 102 is transitioned to the open configuration while the second clamp assembly 104 remains in the closed configuration. After the first fixation component and/or connector is removed or adjusted, the second clamp assembly 104 may be transitioned to the closed configuration by transitioning the first and second outer locking assemblies 114 and 116 to the locked position and/or transitioning the first inner locking member 106 to the locked position. It will be appreciated that the second clamp assembly 104 may be individually controlled to the between the open and closed configuration in a substantially similarly manner as the first clamp assembly 102.

The clamp 100 may be used in a variety of applications, including, but not limited to, external fixation systems for holding bone fragments adjacent to each other.

It will be appreciated that the foregoing description provides examples of the disclosed system and method. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

What is claimed is:
1. A bone fixation clamp comprising:
a shaft including a first shaft end and a second shaft end spaced apart from the first shaft end along a longitudinal axis;

a first clamp assembly coupled to the shaft and transitionable between a first open configuration and a first closed configuration;

a second clamp assembly coupled to the shaft and transitionable between a second open configuration and a second closed configuration, the second clamp being coupled to the first clamp;

a first locking member transitionable between a locked position and an unlocked position, wherein in the locked position the first locking member substantially prevents the first clamp assembly from transitioning from the first closed configuration to the first open configuration;

a locking assembly transitionable between a locked position and an unlocked position, wherein in the locked position the locking assembly substantially prevents both the first clamp assembly from transitioning from the first closed configuration to the first open configuration and the second clamp assembly from transitioning from the second closed configuration to the second open configuration, and wherein in the unlocked position the locking assembly does not prevent the first clamp assembly from transitioning from the first closed configuration to the first open configuration or the second clamp assembly from transitioning from the second closed configuration to the second open configuration;

a first sleeve positioned about the shaft and extending along the longitudinal axis, the first sleeve being rotatably coupled to the first locking member such that rotation of the first locking member about the first sleeve axially translates the first locking member relative to the first sleeve along the longitudinal axis transitioning the first locking member between the locked position and the unlocked position; and wherein rotation of the first locking member about the longitudinal axis transitions the first locking member between the locked position and the unlocked position, wherein the first locking member prevents the first clamp from transitioning from the first closed configuration to the first open configuration when the first locking member is in the locked position and the locking assembly is in the unlocked position, and wherein the locking assembly comprises a first locking sub-assembly and a second locking sub-assembly, the first locking sub-assembly includes a first end component, the second locking sub-assembly includes a second end component spaced apart from the first end component, and wherein the first locking member is spaced from each of the first end component and the second end component along the longitudinal axis.

2. The bone fixation clamp of claim 1, wherein the second clamp assembly is rotatably coupled to the first clamp assembly such that the first clamp assembly is rotatable relative to the second clamp assembly.

3. The bone fixation clamp of claim 1, wherein the first clamp assembly comprises a first c-clamp, and wherein the second clamp assembly comprises a second c-clamp, the first c-clamp having a diameter that is greater than a diameter of the second c-clamp.

4. The bone fixation clamp of claim 1, further comprising:
a second locking member transitionable between a locked position and an unlocked position, wherein in the locked position the second locking member substantially prevents the second clamp assembly from transitioning from the second closed configuration to the first open configuration.

5. The bone fixation clamp of claim 4, wherein the shaft extends along the longitudinal axis from the first end component to the second end component, wherein in the locked position of the locking assembly the first end component provides a force to the first clamp assembly and the second end component provides a force to the second clamp assembly.

6. The bone fixation clamp of claim 5, wherein the first end component is rotatable about the shaft, wherein rotation of the first end component about the shaft transitions the locking assembly between the locked position and the unlocked position.

7. The bone fixation clamp of claim 5, wherein the first locking sub-assembly further includes a first contact member, and the second locking sub-assembly further includes a second contact member, the first contact member being positioned between the first end component and the first clamp assembly such that the first end component provides the force to the first clamp assembly via the first contact member, and the second contact member being positioned between the second end component and the second clamp assembly such that the second end component provides the force to the second clamp assembly via the second contact member,
wherein the first locking member is coupled to the first contact member such that the first locking member is rotationally fixed relative to the first contact member and the first locking member is axially movable relative to the first contact member, and
wherein the second locking member is coupled to the second contact member such that the second locking member is rotationally fixed relative to the second contact member and the second locking member is axially movable relative to the second contact member.

8. The bone fixation clamp of claim 5, further comprising:
a second sleeve positioned about the shaft and extending along the longitudinal axis, the second sleeve being rotatably coupled to the second locking member such that rotation of the second locking member about the second sleeve axially translates the second locking member relative to the second sleeve along the longitudinal axis transitioning the second locking member between the locked position and the unlocked position.

9. The bone fixation clamp of claim 8, wherein the first clamp assembly is positioned about the first sleeve along the longitudinal axis between the first end component and the second end component, and wherein the second clamp assembly is positioned about the second sleeve along the longitudinal axis between the first end component and the second end component, wherein the shaft extends through the first clamp, the first sleeve, the second clamp, and the second sleeve.

10. The bone fixation clamp of claim 9, wherein the first clamp assembly is keyed to the first sleeve such that rotation of the first clamp assembly is fixed relative to the first sleeve.

11. The bone fixation clamp of claim 10, wherein the second sleeve is keyed to the shaft such that rotation of the second sleeve is fixed relative to the shaft.

12. A bone fixation clamp comprising:
a clamp assembly transitionable between an open configuration and a closed configuration; and
a locking member and a contact member configured to individually transition between locked positions and unlocked positions, wherein the clamp assembly is substantially prevented from transitioning from the closed configuration to the open configuration when one of the locking member and the contact member are in the locked position and the other of the locking member and the contact member are in the unlocked position, wherein the locking member is coupled to the contact member such that the locking member is rotationally fixed relative to the contact member and the locking member is axially movable relative to the contact member, wherein the clamp assembly is a first clamp assembly, the locking member is a first locking member, and the contact member is a first contact member, wherein the bone fixation clamp further comprises:
- a second clamp assembly transitionable between an open configuration and a closed configuration;
- a second locking member configured to transition between a locked position and an unlocked position; and
- a second contact member configured to transition between a locked position and an unlocked position, wherein in the locked position of either of the second locking member and the second contact member the second clamp assembly is substantially prevented from transitioning from the closed position to the open position, and wherein the second locking member is coupled to the second contact member such that the second locking member is rotationally fixed relative to the second contact member and the second locking member is axially movable relative to the second contact member, wherein the first and second contact members are transitionable between their respective locked and unlocked positions regardless of the positions of the first and second locking members.

13. The bone fixation clamp of claim 12, further comprising:
first end component; and
a second end component coupled to the first end component,
wherein the first end component engages the first outer locking member and the second end component engages the second outer locking member such that an axial translation of the first end component relative to the second end component transitions both the first and second locking members between their respective locked and unlocked positions.

14. The bone fixation clamp of claim 13, further comprising:
a shaft extending between the first end component and the second end component,
wherein the first end component is rotatable about the shaft, wherein rotation of the first end component about the shaft transitions both the first and second contact members between their respective locked and unlocked positions.

15. A bone fixation clamp comprising:
a shaft including a first shaft end and a second shaft end spaced apart from the first shaft end along a longitudinal axis;
a first clamp sub-assembly coupled to the shaft, the first clamp sub-assembly including a first outer vise plate and a first inner vise plate, the first outer vise plate including a first outer contacting surface having at least one first outer recess, the first inner vise plate including a first inner contacting surface having at least one first inner recess, the first outer vise plate and the first inner vise plate being positioned adjacent to one another along the longitudinal axis such that at least one first receiving cavity is formed by the at least one first outer recess and the at least one first inner recess;
a second clamp sub-assembly coupled to the shaft, the second clamp sub-assembly including a second outer vise plate and a second inner vise plate, the second outer vise plate including a second outer contacting surface having at least one second outer recess, the second inner vise plate including a second inner contacting surface having at least one second inner recess, the second outer vise plate and the second inner vise plate being positioned adjacent to one another along the longitudinal axis such that at least one second receiving cavity is formed by the at least one second outer recess and the at least one second inner recess;
a first inner locking member transitionable between a locked position and an unlocked position, wherein in the locked position the first inner locking member substantially prevents the first outer vise plate from moving relative to the first inner vise plate along the longitudinal axis;
a second inner locking member transitionable between a locked position and an unlocked position, wherein in the locked position the second inner locking member substantially prevents the second outer vise plate from moving relative to the second inner vise plate along the longitudinal axis;
an outer locking sub-assembly transitionable between a locked position and an unlocked position, wherein in the locked position the outer locking sub-assembly substantially prevents both the first outer vise plate from moving relative to the first inner vise plate along the longitudinal axis and the second outer vise plate from moving relative to the second inner vise plate along the longitudinal axis; and
a sleeve positioned about the shaft and extending along the longitudinal axis, the sleeve being rotatably coupled to the first inner locking member such that rotation of the first inner locking member about the sleeve axially translates the first inner locking member relative to the sleeve along the longitudinal axis transitioning the first inner locking member between the locked position and the unlocked position, wherein when the first and second inner locking members are in their respective locked positions and the outer locking sub-assembly is in the unlocked position the first clamp sub-assembly is moveable relative to the second clamp sub-assembly.

16. The bone fixation clamp of claim 15, wherein when the outer locking sub-assembly is in the locked position the first clamp sub-assembly is substantially prevented from rotating relative to the second clamp sub-assembly about the longitudinal axis.

17. The bone fixation clamp of claim 15, wherein a size of the at least one first receiving cavity is greater than a size of the at least one second receiving cavity.

* * * * *